US00RE47255E

(19) United States
(12) Reissued Patent
Rajagopalan et al.

(10) Patent Number: US RE47,255 E
(45) Date of Reissued Patent: *Feb. 26, 2019

(54) PYRAZINE DERIVATIVES AND USES THEREOF IN RENAL MONITORING

(71) Applicant: MediBeacon, Inc., St. Louis, MO (US)

(72) Inventors: Raghavan Rajagopalan, St. Peters, MO (US); Richard B. Dorshow, Saint Charles, MO (US); William L. Neumann, St. Louis, MO (US)

(73) Assignee: MediBeacon, Inc., St. Louis, MO (US)

( * ) Notice: This patent is subject to a terminal disclaimer.

(21) Appl. No.: 15/668,254

(22) Filed: Aug. 3, 2017

Related U.S. Patent Documents

Reissue of:
(64) Patent No.: 9,480,687
Issued: Nov. 1, 2016
Appl. No.: 14/805,048
Filed: Jul. 21, 2015

U.S. Applications:
(60) Continuation of application No. 14/223,042, filed on Mar. 24, 2014, now Pat. No. 9,114,160, which is a division of application No. 13/343,231, filed on Jan. 4, 2012, now Pat. No. 8,722,685, which is a continuation of application No. 11/995,223, filed as application No. PCT/US2007/014370 on Jun. 20, 2007, now Pat. No. 8,115,000, and a continuation-in-part of application No. 11/721,186, filed as application No. PCT/US2005/046732 on Dec. 22, 2005, now Pat. No. 8,778,309.

(60) Provisional application No. 60/815,712, filed on Jun. 22, 2006, provisional application No. 60/638,611, filed on Dec. 23, 2004.

(51) Int. Cl.

| | |
|---|---|
| ***A61K 31/4965*** | (2006.01) |
| ***C07D 241/02*** | (2006.01) |
| ***A61K 31/5377*** | (2006.01) |
| ***A61K 49/00*** | (2006.01) |
| ***C07D 241/26*** | (2006.01) |

(52) U.S. Cl.
CPC ..... *A61K 31/4965* (2013.01); *A61K 31/5377* (2013.01); *A61K 49/0021* (2013.01); *A61K 49/0052* (2013.01); *A61K 49/0054* (2013.01); *C07D 241/26* (2013.01)

(58) Field of Classification Search
CPC ..... A61K 31/4965; A61K 31/5377; A61K 49/0054; A61K 49/0021; A61K 49/0052; C07D 241/26
See application file for complete search history.

(56) References Cited

U.S. PATENT DOCUMENTS

| | | | |
|---|---|---|---|
| 3,808,209 | A | 4/1974 | Donald |
| 3,814,757 | A | 6/1974 | Donald |
| 3,948,895 | A | 4/1976 | Donald |
| 4,517,186 | A | 5/1985 | Johnston |
| 5,395,619 | A | 3/1995 | Zalipsky et al. |
| 5,631,018 | A | 5/1997 | Zalipsky et al. |
| 5,714,342 | A | 2/1998 | Komoriya et al. |
| 6,258,378 | B1 | 7/2001 | Schneider et al. |
| 6,277,403 | B1 | 8/2001 | Mendez et al. |
| 6,406,713 | B1 | 6/2002 | Janoff et al. |
| 6,440,389 | B1 | 8/2002 | Rabito |
| 6,610,322 | B1 | 8/2003 | Keller et al. |

(Continued)

FOREIGN PATENT DOCUMENTS

| | | |
|---|---|---|
| CA | 2340250 | 2/2000 |
| CA | 2340250 A1 | 2/2000 |

(Continued)

OTHER PUBLICATIONS

Abushanab et al., "Studies in the Imidazio[1,5-alpha]pyrazine System", J. Org. Chemistry, 1973, vol. 38, No. 11, pp. 2049-2052.
Achilefu et al., "Novel Receptor-Targeted Fluorescent Contrast Agents for in Vivo Tumor Imaging", Investigative Radiology, 2000, vol. 35, No. 8, pp. 479-485.
Baker et al., "Epidemiology of Trauma Deaths", The American Journal of Surgery, vol. 140, Jul. 1980, pp. 144-150.
Ballou et al., "Tumor labeling in vivo using cyanine-conjugated monoclonal antibodies", Cancer Immunol Immunother, 1995, vol. 41, pp. 257-263.
Cantrell et al., "Repair Synthesis in Human Lymphocytes Provoked by Photolysis of Ethidium Azide", Photochemistry and Photobiology, 1977, vol. 25, pp. 189-191.

(Continued)

*Primary Examiner* — Alan D Diamond
(74) *Attorney, Agent, or Firm* — Armstrong Teasdale LLP

(57) ABSTRACT

The present invention relates to pyrazine derivatives such as those represented by Formulas I and II below.

Formula I

Formula II $X^1$ to $X^4$ of the compounds of Formulas I and II may be characterized as electron withdrawing groups. In contrast, $Y^1$ to $Y^4$ of the compounds of Formulas I and II may be characterized as electron donating groups. Pyrazine derivatives of the present invention may be utilized in assessing renal function. In particular, an effective amount of a pyrazine derivative of the invention may be administered into a body of a patient. The pyrazine derivative that is in the body may be exposed to visible and/or infrared light to cause spectral energy to emanate from the pyrazine derivative. This emanating spectral energy may be detected and utilized to determine renal function of the patient.

21 Claims, 2 Drawing Sheets

(56) References Cited

U.S. PATENT DOCUMENTS

| | | | | |
|---|---|---|---|---|
| 8,115,000 | B2 * | 2/2012 | Rajagopalan | A61K 31/4965 544/407 |
| 8,481,734 | B2 * | 7/2013 | Dorshow | C07D 241/28 544/407 |
| 8,722,685 | B2 * | 5/2014 | Rajagopalan | A61K 31/4965 514/255.06 |
| 2004/0081622 | A1 | 4/2004 | Achilefu et al. | |

FOREIGN PATENT DOCUMENTS

| | | | | |
|---|---|---|---|---|
| DE | 2216925 | | 10/1972 | |
| DE | 10222738 | | 11/2003 | |
| DE | 10222738 | A1 | 11/2003 | |
| EP | 0402472 | | 12/1990 | |
| EP | 0402472 | A1 | 12/1990 | |
| EP | 0579835 | | 1/1994 | |
| EP | 0579835 | A1 | 1/1994 | |
| GB | 2370581 | | 7/2002 | |
| GB | 2370581 | A | 7/2002 | |
| JP | 2017163 | | 1/1990 | |
| JP | 2017163 | A | 1/1990 | |
| JP | 249775 | | 2/1990 | |
| JP | 0249775 | A | 2/1990 | |
| JP | WO9103469 | * | 3/1991 | C07D 241/26 |
| JP | 4112877 | | 4/1992 | |
| JP | 4112877 | A | 4/1992 | |
| JP | 07149736 | | 6/1995 | |
| JP | 07149736 | A | 6/1995 | |
| JP | 07278456 | | 10/1995 | |
| JP | 07278456 | A | 10/1995 | |
| JP | 1997143168 | | 12/1995 | |
| JP | 1997143168 | A | 12/1995 | |
| JP | 1997202765 | | 8/1997 | |
| JP | 1997202765 | A | 8/1997 | |
| JP | 09249773 | | 9/1997 | |
| JP | 09249773 | A | 9/1997 | |
| JP | 1045727 | A | 2/1998 | |
| JP | 10045272 | | 2/1998 | |
| JP | 1998045272 | | 2/1998 | |
| JP | 1999092462 | | 4/1999 | |
| JP | 1999092462 | A | 4/1999 | |
| WO | 8801264 | | 2/1988 | |
| WO | 8801264 | A1 | 2/1988 | |
| WO | 9134469 | A1 | 3/1991 | |
| WO | 199103469 | A1 | 3/1991 | |
| WO | 91/08510 | | 6/1991 | |
| WO | 199108510 | A2 | 6/1991 | |
| WO | 2006026038 | | 3/2006 | |
| WO | 2006026038 | A1 | 3/2006 | |
| WO | 2006071759 | | 7/2006 | |
| WO | 2006071759 | A2 | 7/2006 | |
| WO | 2007106436 | | 9/2007 | |
| WO | 2007106436 | A2 | 9/2007 | |

OTHER PUBLICATIONS

Choyke et al., "Hydrated clearance of gadolinium-DTPA as a measurement of glomerular filtration rate", Kidney International, 1992, vol. 41, pp. 1595-1598.

Doolan et al., "A Clinical Appraisal of the Plasma Concentration and Endogenous Clearance of Creatinine", American Journal of Medicine, 1962, vol. 32, pp. 65-79.

Dorshow et al., "Monitoring physiological function by detection of exogenous fluorescent contrast agents", Part of the SPIE Conference on Optical Diagnostics of Biological Fluids IV, Jan. 1999, SPIE vol. 3599, pp. 2-8.

Dorshow et al., "Noninvasive Fluorescence Detection of Hepatic and Renal Function", Journal of Biomedical Optics, Jul. 1998, vol. 3, No. 3, pp. 340-345.

Dorshow et al., "Non-invasive fluorescence detection of physiological function", Part of the SPIE Conference on Optical diagnostics of Biological Fluids 111, San Jose, California, Jan. 1998, vol. 3252, pp. 124-130.

Dyall et al., "Pyrolysis of Aryl Azides. Xlt Enhanced Neighbouring Group Effects of Carbonyl in a Locked Conformation", Aust. J. Chem., 1992, vol. 45, pp. 1991-2002.

El-Shafei et al., "Synthesis and Reactions of Some Pyrazine Derivatives", Synthetic Communications, 1994, vol. 24, No. 13, pp. 1895-1916.

Fritzberg et al., "Synthesis and Biological Evaluation of Technetium-99m MAG3 as a Hippuran Replacement", The Journal of Nuclear Medicine, 1986, vol. 27, No. 1, pp. 111-116.

Guesry et al., Measurement of glomerular filtration rate by fluorescent excitation of non-radioactive meglumine iothalamate, Clinical Nephrology, 1975, vol. 3, No. 4, pp. 134-138.

Hartman et al., "Synthesis and Reactions of 5,6-Dichloro-3-nitropyrazinamine", Jul.-Aug. 1983, J. Heterocyclic Chem., vol. 20, pp. 1089-1091.

Henry et al. (Ed.), Clinical Diagnosis and Management by Laboratory Methods, 17th Edition, WB Saunders, Philadelphia, PA, 1984, Chapter 1, 28 pages.

Kaminsky et al., Some Congeners and Analogs of Dipyridamole, Journal Med. Chem. Soc., Jul. 1996, vol. 9, pp. 610-612.

Kim et al., "Self-Assembling of Aminopyrazine Fluorescent Dyes and Their Solid State Spectra", Dyes and Pigments, 1998, vol. 39, No. 4, pp. 341-357.

Kim et al., "Self-Assembling of Aminopyrazine Fluorescent Dyes and Their Solid State Spectra", Dyes & Pigments, 1999, vol. 41, pp. 183-191.

Kolendo, "Unusual Product in the Photolysate of 2-Azidoxanthone", Chemistry of Heteroycyclic Compounds, 1998, vol. 34, No. 10, p. 1216.

Lee et al., "Analysis of structure-activity relationships for the 'A-region' of N-(4-t-butylbenzyi)-N'-[4-(methylsulfonylamino)benzyl]thiourea analogues as TRPV1 antagonists", Bioorganic & Medicinal Chemistry Letters, Oxford, GB, 2005, vol. 15, No. 18, pp. 4136-4142.

Lewis et al., "Comparative Evaluation of Urographic Contrast Media, Inulin, and 99mTc-DTPA Clearance Methods for Determination of Glomerular Filtration Rate in Clinical Transplantation", Transplantation, Nov. 1989, vol. 48, pp. 790-796.

Lundqvist et al., "Iohexol Clearance for Renal Function Measurement in Gynaecologic Cancer Patients", Acta Radiologica, 1996, vol. 37, pp. 582-586.

Muller-Suur et al., "Glomerular Filtration and Tubular Secretion of MAG-3 in the Rat Kidney", The Journal of Nuclear Medicine, 1989, vol. 30, No. 12, pp. 1986-1991.

Nally, Jr., "Acute renal failure in hospitalized patients", Cleveland Clinic Journal of Medicine, Jul. 2002, vol. 69, No. 7, pp. 569-574.

Ozaki et al., "Sensitization of Europium(III) Luminescence by DTPA Derivatives", Chemistry Letters, 2000, pp. 312-313.

Pandurangi et al., "Chemistry of Bifunctional Photoprobes. 3. Correlation between the Efficiency of CH Insertion by Photolabile Chelating Agents and Lifetimes of Singlet Nitrenes by Flash Photolysis: First Example of Photochemical Attachment of 99m-Tc-Complex with Human Serum Albumin", J. Org. Chem., 1998, vol. 63, pp. 9019-9030.

Pelegrin et al., "Photoimmunodiagnosis with antibody-fluorescein conjugates: in vitro and in vivo preclinical studies", J. Cell Pharmacol, 1992, vol. 3, pp. 141-145.

Perchais et al., Carboacides Polycyanes—V; Preparation ET Proprietes Des Sels D'AZA-2 Ropenures Polycyanes, Tetrahedron, 1974, vol. 30, pp. 999-1009.

Philbin et al., "Preparation of 2,5-Diamino-3,6-Dinitropyrazine (ANPZ-i): A Novel Candidate High Energy Insensitive Explosive", Propellants, Explosives, Pyrotechnics 25, 2000, pp. 302-306.

Rabito et al., "Renal Function in Patients at Risk of Contrast Material-induced Acute Renal Failure: Noninvasive, Real-Time Monitoring", Radiology, Mar. 1993, vol. 186, pp. 851-854.

Rajagopalan et al., "Polyionic fluorescent bioconjugates as tracer agents for continuous monitoring of renal function", Molecular Imaging: Reporters, Dyes, Markers, and Instrumentation, Proceedings of SPIE, vol. 3924, No. 2000, pp. 28-34.

Regel et al., "Treatment Results of Patients and Multiple Trauma: An Analysis of 3406 Cases Treated between 1972 and 1991 at a German Level I Trauma Center", 1995, vol. 38, No. 1, pp. 70-77.

(56) References Cited

OTHER PUBLICATIONS

Sato, Studies on Pyrazines. 24[1]. A Simple and Versatile Synthetic Method for 3-Aikozy-and 3-Aminopyrazinecarbonitriles, Heteroycyclic Chem., Dec. 1992, vol. 29, pp. 1689-1692.
Shirai et al., "Syntheses and Fluorescent Properties of 2,5-Diamino-3,6-dicyanopyrazine Dyes", Dyes and Pigments, 1998, vol. 39, No. 1, pp. 49-68.
Sohtell et al., "FITC-inulin as a kidney tubule marker in the rat", Acta Physiol Scand, 1983, vol. 119, pp. 313-316.
Tauxe et al. (Ed.), Nuclear Medicine in Clinical Urology and Nephrology, Chapter 6, Tubular Function, Appleton Century Crofts: East Norwalk, 1985, pp. 77-105.
Taylor et al., "Pyrimidopteridines by Oxidative Self-condensation of Aminopyrimidines", Contribution from the Noyes Chemical Laboratory, University of Illinois, and the Welcome Research Laboratories, Apr. 20, 1955, vol. 77, pp. 2243-2248.
Theiler, "Effect of Infrared and Visible Light on 2-Azidoanthraquinone in the QA Binding Site of Photosynthetic Reaction Centres", Biol. Chem. Hoppe-Seyler, Dec. 1986, vol. 367, pp. 1197-1207.
Tilney et al., "Acute Renal Failure in Surgical Patients: Causes, Clinical Patterns, and Care", The Surgical Clinics of North America, Apr. 1983, vol. 63, No. 2, pp. 357-377.
Vanzee et al., "Renal Injury Associated with Intravenous Pyelography in Nondiabetic and Diabetic Patients", Annals of Internal Medicine, 1978, vol. 89, pp. 51-54.
Wang et al., "Design of novel nonlinear optical chromophores with multiple substitutions", Phys. Chem. Chem. Phys., 1999, vol. 1, pp. 3519-3525.
Wentrup, "Hetarylnitrenes-11, Azido/Tetrazoloazine Tautomerisation, and Evidence for Nitrene Formation in the Gas-Phase", Tetrahedron, 1970, vol. 26, pp. 4969-4983.
Taylor et. al., Journal of the American Chemical Society (1955), 77, 2243-8.*
Licha et al., "New contrast Agents for Optical Imaging: Acid-Cleavable conjugates of Cyanine Dyes with Biomolucules", Part of the SPIE conference on Molucular Imaging: Reporters, Dyes, Markers, and Instrumentation, San Jose, California, Jan. 1999, SPIE vol. 3600, pp. 29-35.
Watanabe et al., Synthesis of Some Alkyl- and Arylimidazoles, J. Heterocycl. Chemistry, 1983, vol. 20, pp. 1277-1281 XP002450127.
Moustafa et al., "Synthesis of new pyridoquinoxalines, thienopyridoquinoxalines and pyrimidothienopyridoquinoxalines", Pharmazie, Die, Govi Verlag, Eschborn, DE, 2000, vol. 55, No. 12, pp. 896-899, XP001536673.
Sasalo et al., "Tetrazolo-azido-Isomerisation in Heteroaromatics. I. Syntheses and Reactivities of Some Tetrazolopolyazines", Tetrahedron, 1972, vol. 28, pp. 446-449, XP002450128.
Yu, "Unusual Product in the Photolysate of 2-Azidoxanthone", Chemistry of Heteroycyclic Compounds, 1998, 34(10), p. 1216.
Lobenhoffer et al., "Treatment Results of Patients and Multiple Trauma: An Analysis of 3406 Cases Treated between 1972-1991 at a German Levell Trauma Center", 1995. 38, 70-77.
Coalson, Pathology of Sepsis, Septic Shock and Multiple Organ Failure, Society of Critical Care Medicine, 1986, 27-59.
Cerra, "Multiple Organ Failure Syndrome", In New Horizons, Multiple Organ Failure, 1989, 1-24.
Roch-Ramel et al., Renal excretion and tubular transport of organic anions and cations, in Handbook of Physiology, Section 8, Neurological Physiology, 1992, vol. 11, EE, 189-262.
Nosco et al., "Chemistry of technetium radiopharmaceuticals 1: Chemistry behind the development of technetium-99m compounds to determine kidney function", Coordination ChemistryReviews, 1998, 184, 91·-123.
Ekanoyan et al., In Clinical Practice Guidelines for Chronic Kidney Disease: Evaulation, Classification, and Stratification (KIDOQI) National Kidney Foundation: Washington, DC 2002, 1-22.
Ozaki et al., "Sensitization of Europium(III) Luminescence by DTPA Derivatives", Chemistry Letters, 2000, 312-313.
Dorshow et al., Noninvasive renal function assessment by fluorescence detection, Biomedical Optical Spectroscopy and Diagnostics, Trends in Optics and Photonics Series 22, Sevick-Muraca, Izatt, and Ediger Eidtors, Optical Society_of America, Washington DC, 1998, 54-56.
Barlin, GB, The pyrazines. In the Chemistry of Heterocyclic Compounds., Weissberger and Taylor, Editors, John Wiley & Sons, New York: 1982.
Muller et al., Medical Optical Tomography, SPIE vol. IS11, 1993.
Dorshow et al., "Non-invasive fluorescence detection of hepatic and renal function", Bulletin of the American Physical Society, 1997, vol. 42, No. 1, 681.
Dorshow et al., "Monitoring physiological function by detection of exogenous fluorescent contrast agents", Part of the SPIE Conference on Optical Diagnositics of Biological Fluids IV, Jan. 1999, SPIE vol. 3599, 2-8.
Sato. "Product clas 14: pvrazines", 2004. 16, pp. 751-844.
Zhang et al., "A regioselective synthesis of methyl 7-amino-3-phenylthieno [2m3-b]pyrazine-6-carboxylate", Synthetic Communications, 2001, 32(5), pp. 725-730.
230. Wolfgang Pfeiderer: Ein Beitrag zum Mechanismus der Kondensation von o-Diaminen mit Alloxan und dimethyl-alloxan, Jul. 11, 1955, pp. 1625-1631.
Hnatowich et al., "Radioactive Labeling of Antibody: A Simple and Efficient Method", Science, vol. 220, May 1983, pp. 613-615.
Sandler et al., "AZIDES", Organic Functional Group Preparations, 1986, pp. 323-349.

* cited by examiner

Creatinine (1)
MW: 113 o-Iodohippurate (2)
MW: 327

$^{99m}$Tc-DTPA ( 3)
MW: 487

$^{99m}$Tc-MAG3 (4)
MW: 364

PYRAZINE DERIVATIVES AND USES THEREOF IN RENAL MONITORING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO RELATED APPLICATIONS

This application is a *reissue application of U.S. Pat. No. 9,480,687 B2 which is a* continuation of U.S. application Ser. No. 14/223,042, filed on Mar. 24, 2014 *and issued as U.S. Pat. No. 9,114,160*, which is a divisional of U.S. application Ser. No. 13/343,231, filed on Jan. 4, 2012 and issued as U.S. Pat. No. 8,772,685, which is a continuation of U.S. application Ser. No. 11/995,223, filed on Jan. 10, 2008 and issued as U.S. Pat. No. 8,115,000, which is a U.S. National Stage Application under 35 U.S.C. §371 of International Application No. PCT/US07/14370, filed Jun. 20, 2007, and which claims the benefit of priority to U.S. Provisional Application No. 60/815,712 filed on Jun. 22, 2006; and which is a continuation-in-part of U.S. patent application Ser. No. 11/721,186 filed on Jun. 8, 2007 and issued as U.S. Pat. No. 8,778,309, which is a U.S. National Stage Application under 35 U.S.C. §371 of International Application No. PCT/US2005/046732 filed on Dec. 22, 2005, which claims priority to U.S. Provisional Application No. 60/638,611 filed on Dec. 23, 2004. Each of the above-referenced applications is expressly incorporated by reference herein *in* its entirety.

FIELD OF THE INVENTION

The present invention relates to pyrazine derivatives capable of absorbing and emanating spectral energy in the visible and/or near infrared spectrum. In addition, the present invention relates to methods of using non-radioactive, exogenous agents such as the previously mentioned pyrazine derivatives in medical procedures (e.g., the monitoring of renal function).

BACKGROUND

As a preliminary note, various publications are referenced throughout this disclosure by Arabic numerals in brackets. A citation corresponding to each reference number is listed following the detailed description.

Acute renal failure (ARF) is a common ailment in patients admitted to general medical-surgical hospitals. Approximately half of the patients who develop ARF die, and survivors face marked increases in morbidity and prolonged hospitalization [1]. Early diagnosis is generally believed to be important, because renal failure is often asymptomatic and typically requires careful tracking of renal function markers in the blood. Dynamic monitoring of renal functions of patients is desirable in order to minimize the risk of acute renal failure brought about by various clinical, physiological and pathological conditions [2-6]. Such dynamic monitoring tends to be particularly important in the case of critically ill or injured patients, because a large percentage of these patients tend to face risk of multiple organ failure (MOF) potentially resulting in death [7, 8]. MOF is a sequential failure of the lungs, liver and kidneys and is incited by one or more of acute lung injury (ALI), adult respiratory distress syndrome (ARDS), hypermetabolism, hypotension, persistent inflammatory focus and sepsis syndrome. The common histological features of hypotension and shock leading to MOF generally include tissue necrosis, vascular congestion, interstitial and cellular edema, hemorrhage and microthrombi. These changes generally affect the lungs, liver, kidneys, intestine, adrenal glands, brain and pancreas in descending order of frequency [9]. The transition from early stages of trauma to clinical MOF generally corresponds with a particular degree of liver and renal failure as well as a change in mortality risk from about 30% up to about 50% [10].

Traditionally, renal function of a patient has been determined using crude measurements of the patient's urine output and plasma creatinine levels [11-13]. These values are frequently misleading because such values are affected by age, state of hydration, renal perfusion, muscle mass, dietary intake, and many other clinical and anthropometric variables. In addition, a single value obtained several hours after sampling may be difficult to correlate with other physiologic events such as blood pressure, cardiac output, state of hydration and other specific clinical events (e.g., hemorrhage, bacteremia, ventilator settings and others).

With regard to conventional renal monitoring procedures, an approximation of a patient's glomerular filtration rate (GFR) can be made via a 24 hour urine collection procedure that (as the name suggests) typically requires about 24 hours for urine collection, several more hours for analysis, and a meticulous bedside collection technique. Unfortunately, the undesirably late timing and significant duration of this conventional procedure can reduce the likelihood of effectively treating the patient and/or saving the kidney(s). As a further drawback to this type of procedure, repeat data tends to be equally as cumbersome to obtain as the originally acquired data.

Occasionally, changes in serum creatinine of a patient must be adjusted based on measurement values such as the patient's urinary electrolytes and osmolality as well as derived calculations such as "renal failure index" and/or "fractional excretion of sodium." Such adjustments of serum creatinine undesirably tend to require contemporaneous collection of additional samples of serum and urine and, after some delay, further calculations. Frequently, dosing of medication is adjusted for renal function and thus can be equally as inaccurate, equally delayed, and as difficult to reassess as the measurement values and calculations upon which the dosing is based. Finally, clinical decisions in the critically ill population are often equally as important in their timing as they are in their accuracy.

It is known that hydrophilic, anionic substances are generally capable of being excreted by the kidneys [14]. Renal clearance typically occurs via two pathways: glomerular filtration and tubular secretion. Tubular secretion may be characterized as an active transport process, and hence, the substances clearing via this pathway typically exhibit specific properties with respect to size, charge and lipophilicity.

Most of the substances that pass through the kidneys are filtered through the glomerulus (a small intertwined group of capillaries in the malpighian body of the kidney). Examples of exogenous substances capable of clearing the kidney via glomerular filtration (hereinafter referred to as "GFR agents") are shown in FIG. 1 and include creatinine (1), o-iodohippuran (2), and $^{99m}$Tc-DTPA (3) [15-17]. Examples of exogenous substances that are capable of undergoing renal clearance via tubular secretion include $^{99m}$Tc-MAG3 (4) and other substances known in the art [15, 18, 19].

$^{99m}$Tc-MAG3 (4) is also widely used to assess renal function though gamma scintigraphy as well as through renal blood flow measurement. As one drawback to the substances illustrated in FIG. 1, o-iodohippuran (2), $^{99m}$Tc-DTPA (3) and $^{99m}$Tc-MAG3 (4) include radioisotopes to enable the same to be detected. Even if non-radioactive analogs (e.g., such as an analog of o-iodohippuran (2)) or other non-radioactive substances were to be used for renal function monitoring, such monitoring would typically require the use of undesirable ultraviolet radiation for excitation of those substances.

SUMMARY

In one regard, the present invention relates to transforming lipophilic fluorescent dyes into hydrophilic molecules. One concept of the present invention relates to molecules whose clearance properties are preferably similar to that of creatinine or o-iodohippuran, and to render such molecules hydrophilic by incorporating appropriate polar functionalities such as hydroxyl, carboxyl, sulfonate, phopshonate and the like into their backbones. Pyrazine dyes of the invention may be characterized by some as being desirable for renal applications because they tend to be cleared from the body via the kidneys, demonstrate absorption and emission/fluorescence in the visible region, and tend to exhibit significant Stokes shifts. These properties allow flexibility in both tuning a molecule to a desired wavelength and introducing a variety of substituents to improve clearance properties.

Formula I

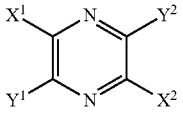

Formula A

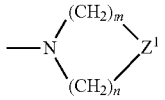

In a first aspect, the present invention is directed to pyrazine derivatives of Formula I. With regard to Formula I, $X^1$ and $X^2$ may be characterized as electron withdrawing substituents and may be independently chosen from the group consisting of —CN, —$CO_2R^1$, —$CONR^2R^3$, —$COR^4$, —$NO_2$, —$SOR^5$, —$SO_2R^6$, —$SO_2OR^7$, —$PO_3R^8R^9$, [—CONH(AA)] —*CO(AA)*, and —CONH (PS). In some embodiments, at least one of $X^1$ and $X^2$ is either [—CONH(AA)] —*CO(AA)* or —CONH(PS). (AA) is *a single natural or unnatural amino acid or* a polypeptide chain that includes [one] *two* or more natural or unnatural α-amino acids linked together by peptide bonds. (PS) is a sulfated or non-sulfated polysaccharide chain that includes one or more monosaccharide units connected by glycosidic linkages. $Y^1$ and $Y^2$ may, at least in some embodiments, be characterized as electron donating substituents and may be independently chosen from the group consisting of —$OR^{10}$, —$SR^{11}$, —$NR^{12}R^{13}$, —$N(R^{14})COR^{15}$, —$P(R^{16})_3$, —$P(OR^{17})_3$, and substituents corresponding to Formula A above. In some embodiments, at least one of $Y^1$ and $Y^2$ is either —$P(R^{16})_3$ or —$P(OR^{17})_3$. $Z^1$ may be a single bond, —$CR^{18}R^{19}$, —O, —$NR^{20}$, —$NCOR^{21}$, —S, —SO and —$SO_2$. $R^1$ to $R^{21}$ may be any suitable substituents capable of providing and/or enhancing desired biological and/or physicochemical properties of pyrazine derivatives of Formula I. For instance, for renal function assessment, each of the R groups of $R^1$ to $R^{21}$ may independently be any one of a hydrogen atom, an anionic functional group (e.g., carboxylate, sulfonate, sulfate, phopshonate and phosphate) or a hydrophilic functional group (e.g., hydroxyl, carboxyl, sulfonyl, sulfonato and phosphonato). As an example, in some embodiments, $R^1$ to $R^{21}$ may independently be selected from the group consisting of —H, —$(CH_2)_aOR^{43}$, —$CH_2(CHOH)_aR^{44}$, —$CH_2(CHOH)_aCO_2H$, —$(CHCO_2H)_aCO_2H$, —$(CH_2)_aNR^{45}R^{46}$, —$CH[(CH_2)_bNH_2]_aCO_2H$, —$CH[(CH_2)_bNH_2]_aCH_2OH$, —$CH_2(CHNH_2)_aCH_2NR^{47}R^{48}$, —$(CH_2CH_2O)_cR^{49}$, —$(CH_2)_dCO(CH_2CH_2O)_cR^{50}$, —$(CH_2)_aSO_3H$, —$(CH_2)_aSO_3^-$, —$(CH_2)_aOSO_3H$, —$(CH_2)_aOSO_3^-$, —$(CH_2)_aNHSO_3H$, —$(CH_2)_aNHSO_3^-$, —$(CH_2)_aPO_3H_2$, —$(CH_2)_aPO_3H^-$, —$(CH_2)_aPO_3^=$, —$(CH_2)_aOPO_3H_2$, —$(CH_2)_aOPO_3H^-$ and —$(CH_2)_aOPO_3$. In such embodiments, each of $R^{43}$ to $R^{50}$ may independently be —H or —$CH_3$. 'a', 'b', 'c', 'd', 'm' and 'n' may be any appropriate integers. For instance, in some embodiments, 'a', 'b', and 'd' may independently vary from 1 to 10, 'c' may vary from 1 to 100, and 'm' and 'n' may independently vary from 1 to 3.

Formula II

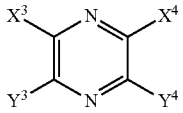

Formula B

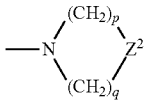

A second aspect of the invention is directed to pyrazine derivatives of Formula II. With regard to Formula II, $X^3$ and $X^4$ may be characterized as electron withdrawing substituents and may be independently chosen from the group consisting of —CN, —$CO_2R^{22}$, —$CONR^{23}R^{24}$, —$COR^{25}$, —$NO_2$, —$SOR^{26}$, —$SO_2R^{27}$, —$SO_2OR^{28}$, —$PO_3R^{29}R^{30}$, [—CONH(AA)] —*CO(AA)*, and —CONH(PS). In some embodiments, at least one of $X^3$ and $X^4$ is either [—CONH(AA)] —*CO(AA)* or —CONH(PS). (AA) is *a single natural or unnatural amino acid or* a polypeptide chain that includes [one] *two* or more natural or unnatural α-amino acids linked together by peptide bonds. (PS) is a sulfated or non-sulfated polysaccharide chain that includes one or more monosaccharide units connected by glycosidic linkages. $Y^3$ and $Y^4$ may, at least in some embodiments, be characterized as electron donating substituents and may be independently chosen from the group consisting of —$OR^{31}$, —$SR^{32}$, —$NR^{33}R^{34}$, —$N(R^{35})COR^{36}$, —$P(R^{37})_3$, —$P(OR^{38})_3$, and substituents corresponding to Formula B above. In some embodiments, at least one of $Y^3$ and $Y^4$ is either —$P(R^{37})_3$ or —$P(OR^{38})_3$. $Z^2$ may be a single bond, —$CR^{39}R^{40}$, —O, —$NR^{41}$, —$NCOR^{42}$, —S, —SO, or —$SO_2$. $R^{22}$ to $R^{42}$ may be any suitable substituents capable of providing and/or enhancing desired biological and/or physicochemical properties of pyrazine derivatives of Formula II. For instance, for renal function assessment, each of the R groups of $R^{22}$ to $R^{42}$ may independently be any one of a hydrogen atom, an anionic functional group (e.g., carboxylate, sulfonate, sulfate, phopshonate and phosphate) or a hydrophilic functional group (e.g., hydroxyl, carboxyl, sulfonyl, sulfonato and phosphonato). As an example, in some embodiments, $R^{22}$ to $R^{42}$ may independently be selected from the group consisting of —H, $—(CH_2)_eOR^{51}$, $—CH_2(CHOH)_eR^{52}$, $—CH_2(CHOH)_eCO_2H$, $—(CHCO_2H)_eCO_2H$, $—(CH_2)_eNR^{53}R^{54}$, $—CH[(CH_2)_fNH_2]_eCO_2H$, $—CH[(CH_2)_fNH_2]_eCH_2OH$, $—CH_2(CHNH_2)_eCH_2NR^{55}R^{56}$, $—(CH_2CH_2O)_gR^{57}$, $—(CH_2)_hCO(CH_2CH_2O)_gR^{58}$, $—(CH_2)_eSO_3H$, $—(CH_2)_eSO_3^-$, $—(CH_2)_eOSO_3H$, $—(CH_2)_eOSO_3^-$, $—(CH_2)_eNHSO_3H$, $—(CH_2)_eNHSO_3^-$, $—(CH_2)_ePO_3H_2$, $—(CH_2)_ePO_3H^-$, $—(CH_2)_ePO_3^=$, $—(CH_2)_eOPO_3H_2$, $—(CH_2)_eOPO_3H^-$ end $—(CH_2)_eOPO_3$. In such embodiments, each of $R^{51}$ to $R^{58}$ may independently be —H or $—CH_3$. 'e', 'f', 'g', 'h', 'p' and 'q' may be any appropriate integers. For instance, in some embodiments, 'e', 'f', and 'h' may independently vary from 1 to 10, 'g' may vary from 1 to 100, and 'p' and 'q' may independently vary from 1 to 3.

Yet a third aspect of the invention is directed to pharmaceutically acceptable compositions, each of which includes one or more pyrazine derivatives disclosed herein. Incidentally, the phrase "pharmaceutically acceptable" herein refers substances which are, within the scope of sound medical judgment, suitable for use in contact with relevant tissues of humans and animals without undue toxicity, irritation, allergic response and the like, and are commensurate with a reasonable benefit/risk ratio. The compositions of this third aspect may include one or more appropriate excipients such as, but not limited to, suitable diluents, preservatives, solubilizers, emulsifiers, adjuvant and/or carriers. One example of a composition of this third aspect may include at least one pyrazine derivative of Formula I and at least one pyrazine derivative of Formula II. Another example of a composition of the third aspect may include one or more pyrazine derivatives of Formula I or one or more pyrazine derivatives of Formula II.

Still a fourth aspect of the invention is directed to methods of determining renal function using pyrazine derivatives such as those described above with regard to Formulas I and II. In these methods, an effective amount of a pyrazine derivative is administered into the body of a patient (e.g., a mammal such as a human or animal subject). Incidentally, an "effective amount" herein generally refers to an amount of pyrazine derivative that is sufficient to enable renal clearance to be analyzed. The pyrazine derivative in the body of the patient is exposed to at least one of visible and near infrared light. Due to this exposure of the pyrazine derivative to the visible and/or infrared light, the pyrazine derivative emanates spectral energy that may be detected by appropriate detection equipment. This spectral energy emanating from the pyrazine derivative may be detected using an appropriate detection mechanism such as an invasive or non-invasive optical probe. Herein, "emanating" or the like refers to spectral energy that is emitted and/or fluoresced from a pyrazine derivative. Renal function can be determined based the spectral energy that is detected. For example, an initial amount of the amount of pyrazine derivative present in the body of a patient may be determined by a magnitude/intensity of light emanated from the pyrazine derivative that is detected (e.g., in the bloodstream). As the pyrazine derivative is cleared from the body, the magnitude/intensity of detected light generally diminishes. Accordingly, a rate at which this magnitude of detected light diminishes may be correlated to a renal clearance rate of the patient. This detection may be done periodically or in substantially real time (providing a substantially continuous monitoring of renal function). Indeed, methods of the present invention enable renal function/clearance to be determined via detecting one or both a change and a rate of change of the detected magnitude of spectral energy (indicative of an amount of the pyrazine derivative that has not been cleared) from the portion of the pyrazine derivative that remains in the body. While this fourth aspect has been described with regard to use of a single pyrazine derivative of the invention, it should be noted that some embodiments of this fourth aspect include the use of compositions of the invention that may include one or more pyrazine derivatives disclosed herein.

DETAILED DESCRIPTION OF SPECIFIC EMBODIMENTS

Formula I

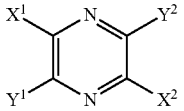

Formula A

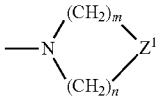

Figure 1:
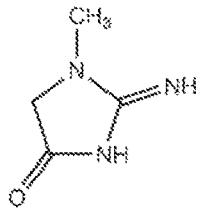
FIG. 1 illustrates some structures of conventional renal agents.
Figure 1:
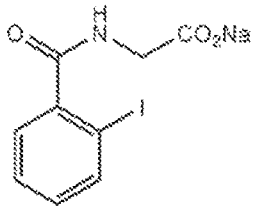
Figure 1:
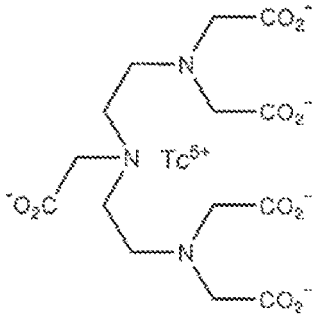
Figure 1:
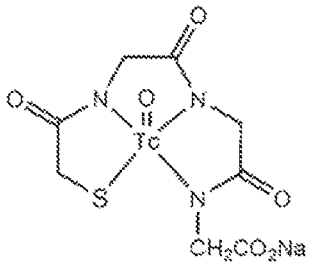

As mentioned above, the present invention includes pyrazine derivatives of Formula I. In a first family of embodiments, $X^1$ and $X^2$ are independently selected from the group consisting of —CN, $—CO_2R^1$, $—CONR^2R^3$, $—COR^4$, $—NO_2$, $—SOR^5$, $—SO_2R^6$, $—SO_2OR^7$, $—PO_3R^8R^9$, [—CONH(AA)] —*CO*(*AA*), and —CONH(PS), wherein at least one of (e.g., one of or both of) $X^1$ and $X^2$ is independently either [—CONH(AA)] —*CO*(*AA*) or —CONH(PS). For instance, in one groups of embodiments, at least one of $X^1$ and $X^2$ is [—CONH(AA)] —*CO*(*AA*). In another group of embodiments, at least one of $X^1$ and $X^2$ is —CONH(PS). With further regard to this first family of embodiments, $Y^1$ and $Y^2$ are independently selected from the group consisting of $—OR^{10}$, $—SR^{11}$, $—NR^{12}R^{13}$, $—N(R^{14})COR^{15}$, $—P(R^{16})_3$, $—P(OR^{17})_3$, and substituents corresponding to Formula A above.

In some embodiments of this first family, $X^1$ and $X^2$ are independently selected from the group consisting of —CN, $—CO_2R^1$, $—CONR^2R^3$, [—CONH(AA)] —*CO*(*AA*), and —CONH(PS), wherein at least one of $X^1$ and $X^2$ is independently either [—CONH(AA)] —*CO*(*AA*) or —CONH(PS). $Y^1$ and $Y^2$ of some embodiments of the first family are independently selected from the group consisting of $—NR^{12}R^{13}$ and substituents corresponding to Formula A above.

In a second family of embodiments, $X^1$ and $X^2$ are independently selected from the group consisting of —CN, $—CO_2R^1$, $—CONR^2R^3$, $—COR^4$, $—NO_2$, $—SOR^5$, $—SO_2R^6$, $—SO_2OR^7$, $—PO_3R^8R^9$, [—CONH(AA)] —*CO*(*AA*), and —CONH(PS). Further, $Y^1$ and $Y^2$ are independently selected from the group consisting of $—OR^{10}$, $—SR^{11}$, $—NR^{12}R^{13}$, $—N(R^{14})COR^{15}$, $—P(R^{16})_3$, $—P(OR^{17})_3$, and substituents corresponding to Formula A above, wherein at least one of (e.g., one of or both of) $Y^1$ and $Y^2$ is independently either $—P(R^{16})_3$ or $—P(OR^{17})_3$. For instance, in one group of embodiments, at least one of $Y^1$ and $Y^2$ is —$P(R^{16})_3$. In another group of embodiments, at least one of $Y^1$ and $Y^2$ is —$P(OR^{17})_3$.

In some embodiments of this second family, $X^1$ and $X^2$ are independently selected from the group consisting of —CN, —$CO_2R^1$, —$CONR^2R^3$; [—CONH(AA)] —*CO(AA)*, and —CONH(PS). In some embodiments of the second family, one of $Y^1$ and $Y^2$ is —$P(R^{16})_3$ or —$P(OR^{17})_3$, and the other of $Y^1$ and $Y^2$ is —$NR^{12}R^{13}$ or a substituent corresponding to Formula A above.

With regard to the above-described first and second families, $Z^1$ is selected from the group consisting of a single bond, —$CR^{18}R^{19}$, —O, —$NR^{20}$, —$NCOR^{21}$, —S, —SO and —$SO_2$. In some embodiments, $Z^1$ is selected from the group consisting of —O, —$NR^{20}$, —S, —SO, and —$SO_2$. In other embodiments, $Z^1$ is selected from the group consisting of —O and —$NR^{20}$.

$R^1$ to $R^{21}$ of the first and second families are independently selected from the group consisting of —H, —$(CH_2)_aOR^{43}$, —$CH_2(CHOH)_aR^{44}$, —$CH_2(CHOH)_aCO_2H$, —$(CHCO_2H)_aCO_2H$, —$(CH_2)_aNR^{45}R^{46}$, —$CH[(CH_2)_bNH_2]_aCO_2H$, —$CH[(CH_2)_bNH_2]_aCH_2OH$, —$CH_2(CHNH_2)_aCH_2NR^{47}R^{48}$, —$(CH_2CH_2O)_cR^{49}$, —$(CH_2)_dCO(CH_2CH_2O)_cR^{50}$, —$(CH_2)_aSO_3H$, —$(CH_2)_aSO_3^-$, —$(CH_2)_aOSO_3H$, —$(CH_2)_aOSO_3^-$, —$(CH_2)_aNHSO_3H$, —$(CH_2)_aNHSO_3^-$, —$(CH_2)_aPO_3H_2$, —$(CH_2)_aPO_3H^-$, —$(CH_2)_aPO_3^=$, —$(CH_2)_aOPO_3H_2$, —$(CH_2)_aOPO_3H^-$ and —$(CH_2)_aOPO_3$. In such embodiments, $R^{43}$ to $R^{50}$ are independently —H or —$CH_3$. In one group of embodiments, $R^1$ to $R^{21}$ of the first and second families are independently selected from the group consisting of —H, —$(CH_2)_aOR^{43}$, —$CH_2(CHOH)_aR^{44}$, —$CH_2(CHOH)_aCO_2H$, —$(CHCO_2H)_aCO_2H$, —$(CH_2)_aNR^{45}R^{46}$, —$CH[(CH_2)_bNH_2]_aCO_2H$, —$CH[(CH_2)_bNH_2]_aCH_2OH$, —$CH_2(CHNH_2)_aCH_2NR^{47}R^{48}$, —$(CH_2CH_2O)_cR^{49}$, —$(CH_2)_dCO(CH_2CH_2O)_cR^{50}$. In another group of embodiments, $R^1$ to $R^{21}$ are independently selected from the group consisting of —H, —$(CH_2)_aOR^{43}$, —$CH_2(CHOH)_aR^{44}$, —$(CH_2)_aNR^{45}R^{46}$, —$(CH_2CH_2O)_cR^{49}$, and —$(CH_2)_dCO(CH_2CH_2O)_dR^{50}$. In still another group of embodiments, $R^1$ to $R^{21}$ are independently selected from the group consisting of —H, —$(CH_2)_aOR^{43}$, —$CH_2(CHOH)_aR^{44}$, —$(CH_2)_aNR^{45}R^{46}$, and —$(CH_2)_dCO(CH_2CH_2O)_dR^{50}$.

Still with regard to these first and second families, 'a', 'b', and 'd' independently vary from 1 to 10, 'c' varies from 1 to 100, and 'm' and 'n' independently varies from 1 to 3. In some embodiments, each of 'a', 'b', and 'd' independently varies from 1 to 6. In some embodiments, 'c' varies from 1 to 20. In some embodiments, 'm' and 'n' are independently 0 or 1.

(AA) is *a single natural or unnatural amino acid of a* polypeptide chain including [one] *two* or more natural or unnatural α-amino acids linked together by peptide bonds. The polypeptide chain (AA) may be a homopolypeptide chain or a heteropolypeptide chain, and may be any appropriate length. For instance, in some embodiments, the polypeptide chain may include [1] *2* to 100 α-amino acid(s), [1] *2* to 90 α-amino acid(s), [1] *2* to 80 α-amino acid(s), [1] *2* to 70 α-amino acid(s), [1] *2* to 60 α-amino acid(s), [1] *2* to 50 α-amino acid(s), [1] *2* to 40 α-amino acid(s), [1] *2* to 30 α-amino acid(s), [1] *2* to 20 α-amino acid(s), or even [1] *2* to 10 α-amino acid(s). In some embodiments, the α-amino acids of the polypeptide chain (AA) are selected from the group consisting of aspartic acid, asparigine, arginine, histidine, lysine, glutamic acid, glutamine, serine, and homoserine. In some embodiments, the α-amino acids of the polypeptide chain (AA) are selected from the group consisting of aspartic acid, glutamic acid, serine, and homoserine. In some embodiments, the [polypeptide chain] (AA) refers to a single amino *acid* (e.g., either aspartic acid or serine).

(PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose).

Formula II

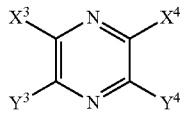

Formula B

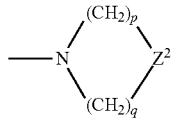

The present invention is also includes pyrazine derivatives corresponding to Formula II above. In a third family of embodiments of the invention, $X^3$ and $X^4$ are independently selected from the group consisting of —CN, —$CO_2R^{22}$, —$CONR^{23}R^{24}$, —$COR^{25}$, —$NO_2$, —$SOR^{26}$, —$SO_2R^{27}$, —$SO_2OR^{28}$, —$PO_3R^{29}R^{30}$, [—CONH(AA)] —*CO(AA)*, and —CONH(PS), wherein at least one of (e.g., one of or both of) $X^3$ and $X^4$ is independently either [—CONH(AA)] —*CO(AA)* or —CONH(PS). For instance, in one groups of embodiments, at least one of $X^3$ and $X^4$ is [—CONH(AA)] —*CO(AA)*. In another group of embodiments, at least one of $X^3$ and $X^4$ is —CONH(PS). With further regard to this first family of embodiments, $Y^3$ and $Y^4$ are independently selected from the group consisting of —$OR^{31}$, —$SR^{32}$, —$NR^{33}R^{34}$, —$N(R^{35})COR^{36}$, —$P(R^{37})_3$, —$P(OR^{38})_3$, and substituents corresponding to Formula B above.

In some embodiments of this third family, $X^3$ and $X^4$ are independently selected from the group consisting of —CN, —$CO_2R^{22}$, —$CONR^{23}R^{24}$, [—$CONH(AA)_r$] —$CO(AA)_r$, and —$CONH(PS)_s$, wherein at least one of $X^3$ and $X^4$ is independently either [—CONH(AA)] —*CO(AA)* or —CONH(PS). $Y^3$ and $Y^4$ of some embodiments of the third family are independently selected from the group consisting of —$NR^{31}R^{32}$ and substituents corresponding to Formula B above.

In still a fourth family of embodiments, $X^3$ and $X^4$ are independently selected from the group consisting of —CN, —$CO_2R^{22}$, —$CONR^{23}R^{24}$, —$COR^{25}$, —$NO_2$, —$SOR^{26}$, —$SO_2R^{27}$, —$SO_2OR^{28}$, —$PO_3R^{29}R^{30}$, [—CONH(AA)]

—*CO*(*AA*), and —CONH(PS). Further, $Y^3$ and $Y^4$ are independently selected from the group consisting of —$OR^{31}$, —$SR^{32}$, —$NR^{33}R^{34}$, —$N(R^{35})COR^{36}$, —$P(R^{37})_3$, —$P(OR^{38})_3$, and substituents corresponding to Formula B above, wherein at least one of $Y^3$ and $Y^4$ is independently either —$P(R^{37})_3$ or —$P(OR^{38})_3$. For instance, in one group of embodiments, at least one of $Y^3$ and $Y^4$ is —$P(R^{37})_3$. In another group of embodiments, at least one of $Y^3$ and $Y^4$ is —$P(OR^{38})_3$.

In some embodiments of this fourth family, $X^3$ and $X^4$ are independently selected from the group consisting of —CN, —$CO_2R^{22}$, —$CONR^{23}R^{24}$, [—CONH(AA)] —*CO*(*AA*), and —CONH(PS). In some embodiments of the fourth family, one of $Y^3$ and $Y^4$ is —$P(R^{37})_3$ or —$P(OR^{38})_3$, and the other of $Y^3$ and $Y^4$ is —$NR^{31}R^{32}$ or a substituent corresponding to Formula B above.

With regard to the above-described third and fourth families, $Z^2$ is selected from the group consisting of a single bond, —$CR^{39}R^{40}$, —O, —$NR^{41}$, —$NCOR^{42}$, —S, —SO, and —$SO_2$. In some embodiments, $Z^2$ is selected from the group consisting of —O, —$NR^{41}$, —S, —SO and —$SO_2$. In some embodiments, $Z^2$ is selected from the group consisting of —O and —$NR^{41}$.

$R^{22}$ to $R^{42}$ are independently selected from the group consisting of —H, —$(CH_2)_eOR^{51}$, —$CH_2(CHOH)_eR^{52}$, —$CH_2(CHOH)_eCO_2H$, —$(CHCO_2H)_eCO_2H$, —$(CH_2)_eNR^{53}R^{54}$, —$CH[(CH_2)_fNH_2]_eCO_2H$, —$CH[(CH_2)_fNH_2]_eCH_2OH$, —$CH_2(CHNH_2)_eCH_2NR^{55}R^{56}$, —$(CH_2CH_2O)_gR^{57}$, —$(CH_2)_hCO(CH_2CH_2O)_gR^{58}$, —$(CH_2)_eSO_3H$, —$(CH_2)_eSO_3^-$, —$(CH_2)_eOSO_3H$, —$(CH_2)_eOSO_3^-$, —$(CH_2)_eNHSO_3H$, —$(CH_2)_eNHSO_3^-$, —$(CH_2)_ePO_3H_2$, —$(CH_2)_ePO_3H^-$, —$(CH_2)_ePO_3^=$, —$(CH_2)_eOPO_3H_2$, —$(CH_2)_eOPO_3H^-$ end —$(CH_2)_eOPO_3$. In such embodiments, $R^{51}$ to $R^{58}$ are independently —H or —$CH_3$. In one group of embodiments, $R^{22}$ to $R^{42}$ are independently selected from the group consisting of —H, —$(CH_2)_eOR^{51}$, —$CH_2(CHOH)_eR^{52}$, —$CH_2(CHOH)_eCO_2H$, —$(CHCO_2H)_eCO_2H$, —$(CH_2)_eNR^{53}R^{54}$, —$CH[(CH_2)_fNH_2]_eCO_2H$, —$CH[(CH_2)_fNH_2]_eCH_2OH$, —$CH_2(CHNH_2)_eCH_2NR^{55}R^{56}$, —$(CH_2CH_2O)_gR^{57}$, and —$(CH_2)_hCO(CH_2CH_2O)_gR^{58}$. In another group of embodiments, $R^{22}$ to $R^{42}$ are independently selected from the group consisting of —H, —$(CH_2)_eOR^{51}$, —$CH_2(CHOH)_eR^{52}$, —$(CH_2)_eNR^{53}R^{54}$, —$(CH_2CH_2O)_gR^{57}$, and —$(CH_2)_hCO(CH_2CH_2O)_gR^{58}$. In still another group of embodiments, $R^{22}$ to $R^{42}$ are independently selected from the group consisting of —H, —$(CH_2)_eOR^{51}$, —$CH_2(CHOH)_eR^{52}$, —$(CH_2)_eNR^{53}R^{54}$, and —$(CH_2)_hCO(CH_2CH_2O)_gR^{58}$.

Still with regard to the third and fourth families, 'e', 'f', and 'h' independently vary from 1 to 10, 'g' varies from 1 to 100, and 'p' and 'q' independently vary from 1 to 3. In some embodiments, 'e', 'f', and 'h' independently vary from 1 to 6. In some embodiments, 'g' varies from 1 to 20. In some embodiments, 'm' and 'n' are independently 0 or 1.

As with the first and second families of embodiments described above, (AA) of the third and fourth families is a *single natural or unnatural amino acid or a* polypeptide chain including [one] *two* or more natural or unnatural α-amino acids linked together by peptide bonds. Accordingly, the description of (AA) with reference to the first and second families of embodiments above applies to (AA) of the third and fourth families of embodiments as well. Likewise, (PS) of the third and fourth families is a sulfated or non-sulfated polysaccharide chain including one or more monosaccharide units connected by glycosidic linkages. As such, the description of (PS) with reference to the first and second families of embodiments above applies to (PS) of the third and fourth families of embodiments as well.

Syntheses of pyrazine derivatives, in general, have been previously studied [27] and described [25, 26, 28, 29]. Preparation procedures for some of the pyrazine derivatives of the present invention, using procedures similar to the above references, are described later in Examples 1 to 11. It is noteworthy that the alkylation of the electron donating amino group in cyano- or carboxypyrazines has a profound effect on electronic transition of the pyrazine chromophore in that the dialkylation of the amino group in 2,5-diamino-3,5-dicyanopyrazine produces large bathochromic shift of about 40-60 nm. It is also noteworthy that the pyrrolidino and piperidio derivatives exhibit substantial difference in their UV spectra in that the former exhibits a bathochromic shift of about 34 nm. These results could be explained on the basis that the highest occupied molecular orbital (HOMO) of the alkylated aminopyrazine is destabilized compared to the parent amino compound. Therefore, based on the above premise, it is predicted that pyrazine derivatives containing highly strained azacycloalkyl substituents, which were not disclosed previously, exhibit larger bathochromic shifts compared to unstrained cyclic analogs.

In accordance with the present invention, one protocol for assessing physiological function of body cells includes administering an effective amount of a pyrazine derivative represented by Formula I or II into a body of a patient. An appropriate dosage of the pyrazine derivate that is administered to the patient is readily determinable by one of ordinary skill in the art and may vary according to the clinical procedure contemplated, generally ranging from about 1 nanomolar to about 100 micromolar. The administration of the pyrazine derivative to the patient may occur in any of a number of appropriate fashions including, but not limited to: (1) intravenous, intraperitoneal, or subcutaneous injection or infusion; (2) oral administration; (3) transdermal absorption through the skin; and (4) inhalation.

Pyrazine derivatives of this invention can be administered as solutions in most pharmaceutically acceptable intravenous vehicles known in the art. Pharmaceutically acceptable vehicles that are well known to those skilled in the art include, but are not limited to, 0.01-0.1 M phosphate buffer or 0.8% saline. Additionally, pharmaceutically acceptable carriers may be aqueous or non-aqueous solutions, suspensions, emulsions, or appropriate combinations thereof. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Exemplary parenteral vehicles include sodium chloride solution, Ringer's dextrose, dextrose and sodium chloride, lactated Ringer's or fixed oils. Exemplary intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Suitable diluents, preservatives, solubilizers, emulsifiers, adjuvant and/or carriers are also suitable excipients. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions may likely influence the physical state, solubility, stability, rate of in vivo release, and/or rate of in vivo clearance.

Still referring to the above-mentioned protocol, the pyrazine derivative is exposed to visible and/or near infrared light. This exposure of the pyrazine derivate to light may occur at any appropriate time but preferably occurs while the pyrazine derivative is located in the body. Due to this exposure of the pyrazine derivate to the visible and/or infrared light, the pyrazine derivate emanates spectral energy (e.g., visible and/or near infrared light) that may be detected by appropriate detection equipment. The spectral energy emanated from the pyrazine derivative tends to exhibit a wavelength range greater than a wavelength range absorbed by the pyrazine derivative. For example, if an embodiment of the pyrazine derivative absorbs light of about 700 nm, the pyrazine derivative may emit light of about 745 nm.

Detection of the pyrazine derivate (or more particularly, the light emanating therefrom) may be achieved through optical fluorescence, absorbance or light scattering procedures known in the art. In one embodiment, this detection of the emanated spectral energy may be characterized as a collection of the emanated spectral energy and a generation of electrical signal indicative of the collected spectral energy. The mechanism(s) utilized to detect the spectral energy from the pyrazine derivative that is present in the body may be designed to detect only selected wavelengths (or wavelength ranges) and/or may include one or more appropriate spectral filters. Various catheters, endoscopes, ear clips, hand bands, head bands, surface coils, finger probes and the like may be utilized to expose the pyrazine derivative to light and/or to detect the light emanating therefrom [30]. This detection of spectral energy may be accomplished at one or more times intermittently or may be substantially continuous.

Renal function of the patient can be determined based on the detected spectral energy. This can be achieved by using data indicative of the detected spectral energy and generating an intensity/time profile indicative of a clearance of the pyrazine derivative from the body. This profile may be correlated to a physiological or pathological condition. For example, the patient's clearance profiles and/or clearance rates may be compared to known clearance profiles and/or rates to assess the patient's renal function and to diagnose the patient's physiological condition. In the case of analyzing the presence of the pyrazine derivative in bodily fluids, concentration/time curves may be generated and analyzed (preferably in real time) using an appropriate microprocessor to diagnose renal function.

Physiological function can be assessed by: (1) comparing differences in manners in which normal and impaired cells remove a pyrazine derivative of the invention from the bloodstream; (2) measuring a rate or an accumulation of a pyrazine derivative of the invention in the organs or tissues; and/or (3) obtaining tomographic images of organs or tissues having a pyrazine derivative of the invention associated therewith. For example, blood pool clearance may be measured non-invasively from convenient surface capillaries such as those found in an ear lobe or a finger or can be measured invasively using an appropriate instrument such as an endovascular catheter. Accumulation of a pyrazine derivative of the invention within cells of interest can be assessed in a similar fashion.

A modified pulmonary artery catheter may also be utilized to, inter alia, make the desired measurements [32] of spectral energy emanating from a pyrazine derivative of the invention. The ability for a pulmonary catheter to detect spectral energy emanating from a pyrazine derivative of the invention is a distinct improvement over current pulmonary artery catheters that measure only intravascular pressures, cardiac output and other derived measures of blood flow. Traditionally, critically ill patients have been managed using only the above-listed parameters, and their treatment has tended to be dependent upon intermittent blood sampling and testing for assessment of renal function. These traditional parameters provide for discontinuous data and are frequently misleading in many patient populations.

Modification of a standard pulmonary artery catheter only requires making a fiber optic sensor thereof wavelength-specific. Catheters that incorporate fiber optic technology for measuring mixed venous oxygen saturation exist currently. In one characterization, it may be said that the modified pulmonary artery catheter incorporates a wavelength-specific optical sensor into a tip of a standard pulmonary artery catheter. This wavelength-specific optical sensor can be utilized to monitor renal function-specific elimination of a designed optically detectable chemical entity such as the pyrazine derivatives of the present invention. Thus, by a method analogous to a dye dilution curve, real-time renal function can be monitored by the disappearance/clearance of an optically detected compound.

The following examples illustrate specific embodiments of the invention. As would be apparent to skilled artisans, various changes and modifications are possible and are contemplated within the scope of the invention described.

EXAMPLE 1

Preparation of 3,6-diamino-$N^2$,$N^2$,$N^5$,$N^5$-tetrakis(2-methoxyethyl)pyrazine-2,5-dicarboxamide

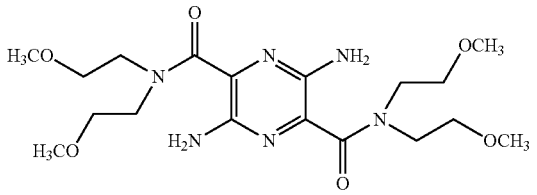

A mixture of 3,6-diaminopyrazine-2,5-dicarboxylic acid (200 mg, 1.01 mmol), bis-2-(methoxyethyl)amine (372 μL, 335.5 mg, 2.52 mmol), HOBt-$H_2O$ (459 mg, 3.00 mmol), and EDC-HCl (575 mg, 3.00 mmol) were stirred together in DMF (20 mL) for 1 h at room temperature. The mixture was concentrated to dryness and the residue was partitioned with EtOAc and water. The layers were separated and the EtOAc solution was washed with saturated $NaHCO_3$ and brine. The solution was dried over anhydrous $Na_2SO_4$, filtered and concentrated. Purification by radial flash chromatography ($SiO_2$, 10/1 $CHCl_3$-MeOH) afforded 228.7 mg (53% yield) of Example 1 as an orange foam: $^1$H NMR (300 MHz, $CDCl_3$), δ 4.92 (s, 4H), 3.76 (apparent t, J=5.4 Hz, 4H), 3.70

(apparent t, J=5.6 Hz, 4H), 3.64 (apparent t, J=5.4 Hz, 4H), 3.565 (apparent t, J=5.4 Hz), 3.67 (s, 6H), 3.28 (s, 6H). $^{13}$C NMR (75 MHz, $CDCl_3$) δ 167.6 (s), 145.6 (s), 131.0 (s), 72.0 (t), 70.8 (t), 59.2 (q), 49.7 (t), 47.1 (t). LCMS (5-95% gradient acetonitrile in 0.1% TFA over 10 min), single peak retention time=3.14 min on 30 mm column, $(M+H)^+$=429. UV/vis (100 μM in PBS) $\lambda_{abs}$=394 nm. Fluorescence (100 nm) $\lambda_{ex}$=394 nm $\lambda_{em}$=550 nm.

EXAMPLE 2

3,6-diamino-N$^2$,N$^5$-bis(2,3-dihydroxydrodyl)dyrazine-2,5-dicarboxamide

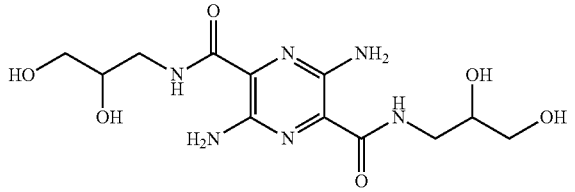

Step 1. Synthesis of 3,6-diamino-N$^2$,N$^5$-bis((2,2-dimethyl-1,3-dioxolan-4-yl)methyl)pyrazine-2,5-dicarboxamide

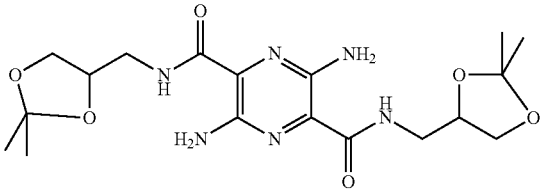

A mixture of 3,6-diaminopyrazine-2,5-dicarboxylic acid (350 mg, 1.77 mmol), racemic (2,2-dimethyl-1,3-dioxolan-4-yl)methanamine (933 μL, 944 mg, 7.20 mmol), HOBt-$H_2O$ (812 mg, 5.3 mmol), and EDC-HCl (1.02 g, 5.32 mmol) were stirred together in DMF (20 mL) for 16 h at room temperature. The mixture was concentrated to dryness and the residue was partitioned with EtOAc and water. The layers were separated and the EtOAc solution was washed with saturated $NaHCO_3$ and brine. The solution was dried over anhydrous $Na_2SO_4$, filtered and concentrated to afford 665 mg (88% yield) of the bis-amide diastereomeric pair as a yellow solid: $^1$NMR (300 MHz, $CDCl_3$) δ 8.38 (t, J=5.8 Hz, 2H), 6.55 (s, 4H), 4.21 (quintet, J=5.8 Hz, 2H), 3.98 (dd, J=8.4 Hz, 6.3 Hz, 2H), 3.65 (dd, J=8.4 Hz, J=5.8 Hz, 2H), 3.39 (apparent quartet—diastereotopic mixture, J=5.9 Hz, 4H), 1.35 (s, 6H), 1.26 (s, 6H). $^{13}$C NMR (75 MHz, $CDCl_3$) δ 165.7 (s), 146.8 (s), 126.8 (s), 109.2 (s), 74.8 (d), 67.2 (t), 42.2, 41.1 (t—diastereotopic pair), 27.6 (q), 26.1 (q).

Step 2

The product from Step 1 was dissolved in THF (100 mL) and treated with 1.0 N HCl (2 mL). After hydrolysis was complete, the mixture was treated with $K_2CO_3$ (1 g) and stirred for 1 h and filtered through a plug of C18 with using methanol. The filtrate was concentrated to dryness and the residue was triturated with MeOH (50 mL). The solids were filtered and discarded and the residue was treated with ether (50 mL). The precipitate was collected by filtration and dried at high vacuum. This material was purified by radial flash chromatography to afford 221 mg (36% yield) of Example 2 as a orange solid: $^1$NMR (300 MHz, DMSO-$d_6$) δ 8.00 (bm, 6H), 5.39 (bs, 2H), 4.88 (bs, 2H), 3.63-3.71 (complex m, 2H), 3.40 (dd, J=11.1, 5.10 Hz, 2H), 3.28 (dd, J=11.1, 6.60 Hz, 2H), 2.92 (dd, J=12.6, 3.3 Hz, 2H), 2.65 (dd, J=12.6, 8.4 Hz, 2H). LCMS (5-95% gradient acetonitrile in 0.1% TFA over 10 min), single peak retention time=4.13 min on 30 mm column, $(M+H)^+$=345. UV/vis (100 μM in $H_2O$) $\lambda_{abs}$=432 nm. Fluorescence $\lambda_{ex}$=432 nm, $\lambda_{em}$=558 nm.

EXAMPLE 3

3,6-Diamino-N$^2$,N$^5$-bis(serine)-pyrazine-2,5-dicarboxamide

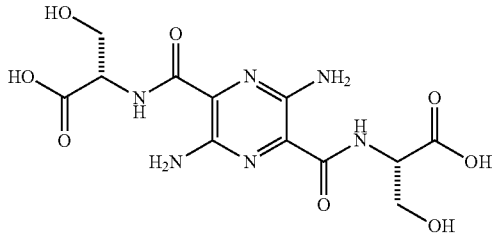

Step 1. Synthesis of 3,6-Diamino-N$^2$,N$^5$-bis(O-benzylserine methyl ester)-pyrazine-2,5-dicarboxamide

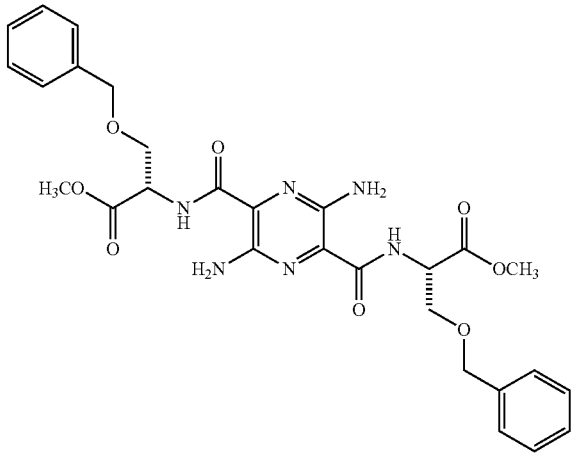

A mixture of sodium 3,6-diaminopyrazine-2,5-dicarboxylate (300 mg, 1.24 mmol), Ser(OBn)-OMe-HCl salt (647 mg, 2.64 mmol), HOBt-$H_2O$ (570 mg, 3.72 mmol) and EDC-HCl (690 mg, 3.60 mmol) in DMF (25 mL) was treated with TEA (2 mL). The resulting mixture was stirred for 16 h and concentrated. Work up as in Example 1 afforded 370 mg (51% yield) of the bisamide as a bright yellow powder: $^1$NMR (300 MHz, $CDCl_3$) δ 8.47 (d, J=8.74 Hz, 2H), 7.25-7.37 (complex m, 10H), 5.98 (bs, 4H), 4.85 (dt, J=8.7, 3.3 Hz, 2H), 4.56 (ABq, J=12.6, Hz, Δν=11.9 Hz, 4H), 3.99 (one half of an ABq of d, J=8.7, 3.3, Δν obscured, 2H), 3.76-3.80 (one half of an ABq obscured, 2H), 3.78 (s, 6H). 13C NMR (75 MHz, CDCl3) 170.5 (s), 165.1 (s), 146.8 (s), 138.7 (s) 128.6 (d), 128.1 (d), 127.8 (d), 126.9 (s), 73.5 (t), 69.8 (t), 53.0 (q), 52.9 (q). LCMS (5-95% gradient acetonitrile in 0.1% TFA over 10 min), single peak retention time=4.93 min on 30 mm column, (M+H)+=581.

Step 2. Synthesis of 3,6-Diamino-$N^2$,$N^5$-bis(O-benzylserine)-pyrazine-2,5-dicarboxamide

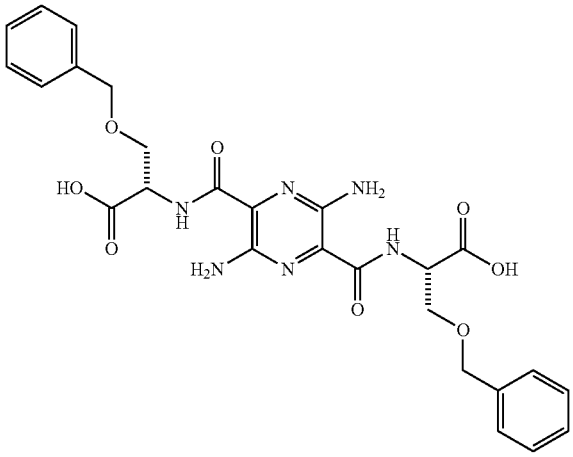

The product from step 1 (370 mg, 0.64 mmol) in THF (10 mL) was treated with 1.0 N sodium hydroxide (2.5 mL). After stirring at room temperature for 30 min, the reaction was judged complete by TLC. The pH was adjusted to approximately 2 by the addition of 1.0 N HCl and the resulting solution was extracted (3×) with EtOAc. The layers were combined, dried over sodium sulfate, filtered and concentrated to afford 353 mg (100% yield) of the diacid as an orange foam: LCMS (5-95% gradient acetonitrile in 0.1% TFA over 10 min), retention time=4.41 min on 30 mm column, $(M+H)^+$=553.

Step 3

To the product from step 2 (353 mg, 0.64 mmol) in methanol (20 mL) was added 5% Pd/C (300 mg) and ammonium formate (600 mg). The resulting reaction was heated at reflux for 2 h. The reaction was cooled to room temperature, filtered through a plug of celite and concentrated. The residue was recrystallized from methanol-ether to provide 191 mg (80% yield) of Example 3 as a yellow foam: $^1$NMR (300 MHz, DMSO-$d_6$) δ 8.48 (d, J=6.9 Hz, 2H), 6.72 (bs, 4H), 3.95 (apparent quartet, J=5.1 Hz, 2H), 3.60 (apparent ABq of doublets; down-field group centered at 3.71, J=9.9, 5.1 Hz, 2H; up-field group centered at 3.48, J=9.9, 6.3 Hz, 2H). $^{13}$C NMR (75 MHz, CDCl3) δ 172.9 (s), 164.9 (s), 147.0 (s), 127.0 (s), 62.9 (d), 55.7 (t). LCMS (5-95% gradient acetonitrile in 0.1% TFA over 10 min), single peak retention time=1.45 min on 30 mm column, $(M+H)^+$=373. UV/vis (100 μM in PBS) $\lambda_{abs}$=434 nm. Fluorescence $\lambda_{ex}$=449 nm, $\lambda_{em}$=559 nm.

EXAMPLE 4

3,6-bis(bis(2-methoxyethyl)amino)-$N^2$,$N^2$,$N^5$,$N^5$-tetrakis(2-methoxyethyl) pyrazine-2,5-dicarboxamide bis TFA salt

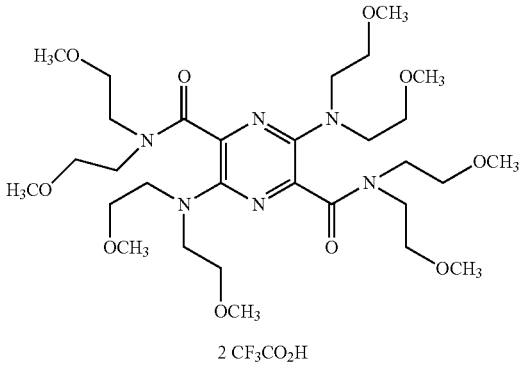

Step 1. Synthesis of 3,6-dibromopyrazine-2,5-dicarboxylic acid

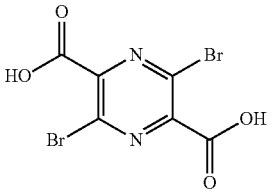

3,6-Diaminopyrazine-2,5-dicarboxylic acid (499 mg, 2.52 mmol) was dissolved in 48% hydrobromic acid (10 mL) and cooled to 0° C. in an ice-salt bath. To this stirred mixture was added a solution of sodium nitrite (695 mg, 10.1 mmol) in water (10 mL) dropwise so that the temperature remains below 5° C. The resulting mixture was stirred for 3 h at 5-15° C., during which time the red mixture became a yellow solution. The yellow solution was poured into a solution of cupric bromide (2.23 g, 10.1 mmol) in water (100 mL) and the resulting mixture was stirred at room temperature. After an addition 3 h, the aqueous mixture was extracted with EtOAc (3×). The combined extracts were dried ($Na_2SO_4$), filtered and concentrated to afford 440 mg (54% yield) 3,6-dibromopyrazine-2,5-dicarboxylic acid as a pale yellow solid: $^{13}$C NMR (75 MHz, CDCl3) δ 164.3 (s), 148.8 (s), 134.9 (s). HPLC (5-95% gradient acetonitrile in 0.1% TFA over 10 min), single peak retention time=2.95 min on 250 mm column.

Step 2. Synthesis of 3-(Bis(2-methoxyethyl)amino)-6-bromo-$N^2$,$N^2$,$N^5$,$N^5$-tetrakis(2-methoxyethyl) pyrazine-2,5-dicarboxamide

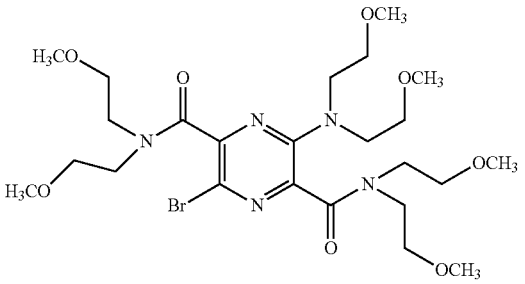

The product from step 1 (440 mg, 1.36 mmol) was dissolved in DMF (25 mL), treated with HOBt-$H_2O$ (624 mg, 4.08 mmol), and EDC-HCl (786 mg, 4.10 mmol) and stirred for 30 min at room temperature. Bis(2-methoxylethyl)amine (620 mL, 559 mg, 4.20 mmol) was added and the resulting mixture was stirred at room temperature for 16 h and concentrated. The residue was partitioned with water and EtOAc. The EtOAc layer was separated and the aqueous was extracted again with EtOAc. The combined organic layers were washed with 0.5 N HCl, saturated sodium bicarbonate, and brine. The organic layer was dried ($Na_2SO_4$), filtered and concentrated to afford 214 mg of 3-(bis(2-methoxyethyl)amino)-6-bromo-$N^2$,$N^2$,$N^5$,$N^5$-tetrakis(2-methoxyethyl)pyrazine-2,5-dicarboxamide (26% yield) as a brown oil: LCMS (5-95% gradient acetonitrile in 0.1% TFA over 10 min), single peak retention time=3.85 min on 30 mm column, $(M+H)^+$=608.

Step 3

To the product from step 2 (116 mg, 0.19 mmol) was added bis(2-methoxylethyl)amine (3.0 mL, 2.71 g, 20.3 mmol) and a "spatula tip" of $Pd(PPh_3)_4$. The resulting mixture was heated to 140° C. for 2 h. The reaction was cooled and concentrated. The residue was purified by flash chromatography ($SiO_2$, 10/1 $CHCl_3$-MeOH). The resulting material was purified again by reverse phase medium pressure chromatography (C18, 10-50% manual gradient acetonitrile in 0.1% TFA) to afford 12 mg (10% yield) of Example 4 as an orange-brown film: LCMS (15-95% gradient acetonitrile in 0.1% TFA over 10 min), single peak retention time=3.85 min on 250 mm column, $(M+H)^+$=661. UV/vis (100 μM in PBS) $\lambda_{abs}$=434 nm. Fluorescence $\lambda_{ex}$=449 nm, $\lambda_{em}$=559 nm.

EXAMPLE 5

3,6-diamino-$N^2$,$N^5$-bis(2-aminoethyl)pyrazine-2,5-dicarboxamide bis TFA salt

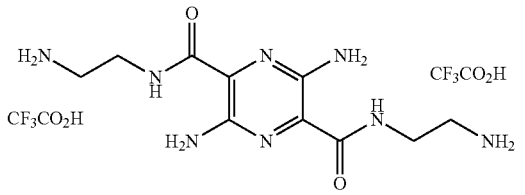

Step 1. Synthesis of 3,6-diamino-$N^2$,$N^5$-bis[2-(tert-butoxycarbonyl)aminoethyl]pyrazine-2,5-dicarboxamide

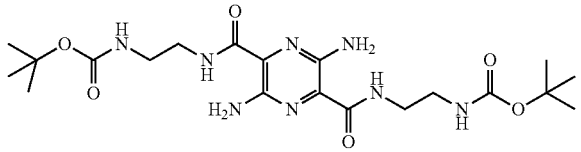

A mixture of sodium 3,6-diaminopyrazine-2,5-dicarboxylate (500 mg, 2.07 mmol), tert-butyl 2-aminoethylcarbamate (673 mg, 4.20 mmol), HOBt-$H_2O$ (836 mg, 5.46 mmol) and EDC-HCl (1.05 g, 5.48 mmol) in DMF (25 mL) was stirred for 16 h and concentrated. Work up as in Example 1 afforded 770 mg (76% yield) of the bisamide as an orange foam: $^1$NMR (300 MHz, DMSO-$d_6$) major comformer, δ 8.44 (t, J=5.7 Hz, 2H), 6.90 (t, J=5.7 Hz, 2H), 6.48 (bs, 4H), 2.93-3.16 (complex m, 8H), 1.37 (s, 9H), 1.36 (s, 9H). $^{13}$C NMR (75 MHz, DMSO-$d_6$), conformational isomers δ 165.1 (s), 155.5 (bs), 155.4 (bs), 146.0 (s), 126.2 (s), 77.7 (bs), 77.5 (bs), 45.2 (bt), 44.5 (bt), 28.2 (q).

Step 2

To the product from step 1 (770 mg, 1.60 mmol) in methylene chloride (100 mL) was added TFA (25 mL) and the reaction was stirred at room temperature for 2 h. The mixture was concentrated and the residue taken up into methanol (15 mL). Ether (200 mL) was added and the orange solid precipitate was isolated by filtration and dried at high vacuum to afford 627 mg (77% yield) of Example 5 as an orange powder: $^1$NMR (300 MHz, DMSO-$d_6$) δ 8.70 (t, J=6 Hz, 2H), 7.86 (bs, 6H), 6.50 (bs, 4H), 3.46-3.58 (m, 4H), 3.26-3.40 (m, 4H). $^{13}$C NMR (75 MHz, DMSO-$d_6$) δ 166.4 (s), 146.8 (s), 127.0 (s), 39.4 (t), 37.4 (t). LCMS (5-95% gradient acetonitrile in 0.1% TFA over 10 min), single peak retention time=3.62 min on 30 mm column, $(M+H)^+$=283. UV/vis (100 μM in PBS) $\lambda_{abs}$=435 nm. Fluorescence (100 nM) $\lambda_{ex}$=449 nm, $\lambda_{em}$=562 nm.

EXAMPLE 6

3,6-Diamino-$N^2$,$N^5$-bis(D-Aspartate)-pyrazine-2,5-dicarboxamide

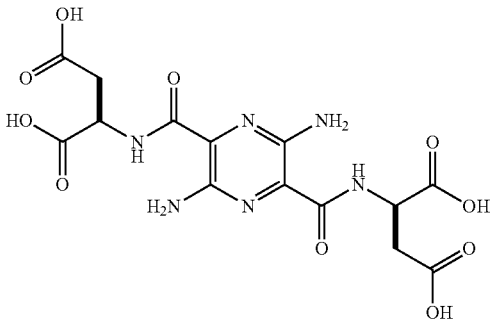

Step 1. Synthesis of 3,6-Diamino-$N^2$,$N^5$-bis(benzyl D-Obenzyl-Aspartate)-pyrazine-2,5-dicarboxamide

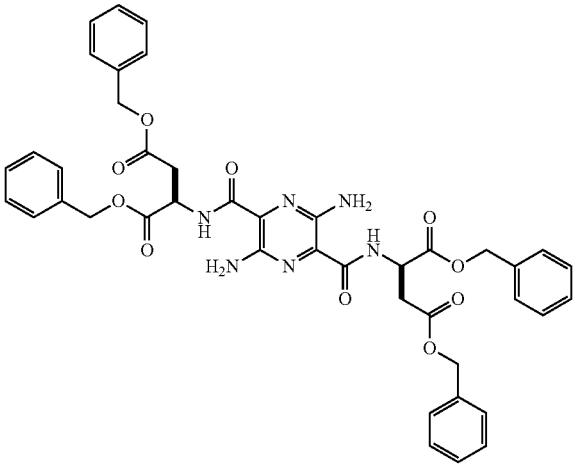

A mixture of sodium 3,6-diaminopyrazine-2,5-dicarboxylate (600 mg, 2.48 mmol), Asp(OBn)-OMe-p-TosH salt (2.43 g, 5.00 mmol), HOBt-$H_2O$ (919 mg, 6.00 mmol) and EDC-HCl (1.14 g, 5.95 mmol) in DMF (50 mL) was treated with TEA (4 mL). The resulting mixture was stirred over night at room temperature. The reaction mixture was concentrated and the residue was partitioned with water and EtOAc. The EtOAc layer was separated and washed successively with saturated sodium bicarbonate, water and brine. The EtOAc solution was dried ($Na_2SO_4$), filtered and concentrated. The residue was purified by flash chromatography ($SiO_2$, 50/1 $CHCl_3$-MeOH to 10/1) to afford 1.15 g of the bis-amide (58% yield) as a yellow foam: $^1$NMR (500 MHz, $CDCl_3$) δ 8.61 (d, J=8.4 Hz, 2H), 7.29-7.39 (m, 20H), 5.85 (bs, 4H), 5.22 (ABq, J=10.0 Hz, Δν=17.3 Hz, 4H), 5.10 (ABq, J=12.2 Hz, Δν=34.3 Hz, 4H), 5.06-5.09 (obs m, 2H), 3.11 (ABq of d, J=17.0, 5.14 Hz, Δν=77.9 Hz, 4H). $^{13}$C NMR (75 MHz, $CDCl_3$) δ 170.7 (s), 170.7 (s), 165.4 (s), 147.0 (s), 135.7 (s), 135.6 (s), 129.0 (d), 128.9 (d), 128.8 (d), 128.75 (d), 128.7 (d), 126.9 (s), 68.0 (t), 67.3 (t), 49.1 (d), 37.0 (t). LCMS (50-95% gradient acetonitrile in 0.1% TFA over 10 min), single peak retention time=5.97 min on 250 mm column, $(M+H)^+$=789.

Step 2

To the product from step 1 (510 mg, 0.65 mmol) was added THF (20 mL) and water (10 mL). The this stirred mixture was added 10% Pd(C) (500 mg) and ammonium formate (1 g). The resulting mixture was heated to 60° C. for 2 h and allowed to cool to room temperature. The mixture was filtered through celite and concentrated. The resulting material was purified again by reverse phase medium pressure chromatography (C18, 10-70% manual gradient acetonitrile in 0.1% TFA) to afford 137.8 mg (54% yield) of Example 6 as an orange solid: $^1$NMR (300 MHz, DMSO-$d_6$) δ 8.62 (d, J=8.4 Hz, 2H), 6.67 (bs, 4H), 4.725 (dt, J=8.4, 5.4 Hz, 2H), 2.74-2.88 (complex m, 4H). $^{13}$C NMR (75 MHz, DMSO-$d_6$) δ 172.6 (s), 165.2 (s), 147.0 (s), 126.6 (s), 60.8 (t), 49.1 (d). LCMS (5-95% gradient acetonitrile in 0.1% TFA over 10 min), single peak retention time=4.01 min on 250 mm column, $(M+H)^+$=429. UV/vis (100 μM in PBS) $\lambda_{abs}$=433 nm. Fluorescence (100 nM) $\lambda_{ex}$=449 nm, $\lambda_{em}$=558 nm.

EXAMPLE 7

3,6-Diamino-$N^2$,$N^5$-bis(14-oxo-2,5,8,11-tetraoxa-15-azaheptadecan-17-yl) pyrazine-2,5-dicarboxamide

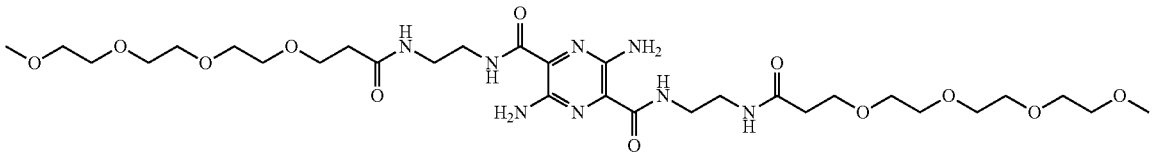

To a solution of Example 5 (77.4 mg, 0.15 mmol) in DMF (5 mL) was added TEA (151 mg, 1.49 mmol) and 2,5-dioxopyrrolidin-1-yl 2,5,8,11-tetraoxatetradecan-14-oate (113 mg, 0.34 mmol) and the reaction was stirred for 16 h at room temperature. The reaction was concentrated and the residue was purified by medium pressure revered phase chromagraphy (LiChroprep RP-18 Lobar (B) 25×310 mm—EMD chemicals 40-63 μm, ~70 g, 90/10 to 80/20 0.1% TFA-ACN) to afford 37.4 mg (35% yield) of example 7 as an orange film: $^1$NMR (300 MHz, DMSO-$d_6$) δ 8.47 (t, J=5.7 Hz, 2H), 7.96 (t, J=5.4 Hz, 2H), 3.20-3.60 (complex m, 36H), 3.47 (s, 3H), 3.46 (s, 3H), 2.30 (t, J=6.3 Hz, 4H). $^{13}$C NMR (75 MHz, DMSO-$d_6$) δ 170.2 (s), 165.1 (s), 146.0 (s), 126.2 (s), 71.2 (t), 69.7 (t), 69.6 (t), 69.5 (t), 69.4 (t), 66.7 (t), 58.0 (q), 38.2 (t), 36.2 (t). LCMS (5-95% gradient acetonitrile in 0.1% TFA over 10 min), single peak retention time=4.01 min on 250 mm column, $(M+H)^+$=719, $(M+Na)^+$=741. UV/vis (100 μM in PBS) $\lambda_{abs}$=437 nm. Fluorescence (100 nM) $\lambda_{ex}$=437 nm, $\lambda_{em}$=559 nm.

EXAMPLE 8

3,6-Diamino-$N^2$,$N^5$-bis(26-oxo-2,5,8,11,14,17,20,23-octaoxa-27-azanonacosan-29-yl)pyrazine-2,5di-carboxamide

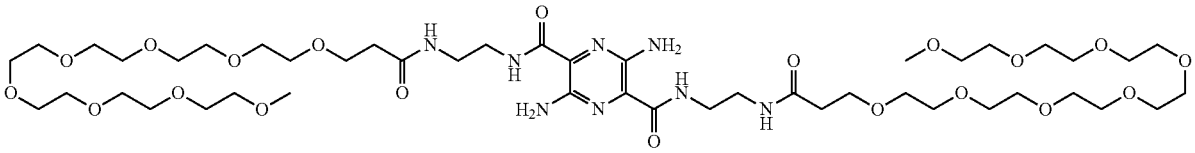

To a solution of Example 5 (50.3 mg, 0.10 mmol) in DMF (5 mL) was added TEA (109 mg, 1.08 mmol) and 2,5-dioxopyrrolidin-1-yl 2,5,8,11,14,17,20,23-octaoxahexacosan-26-oate (128 mg, 0.25 mmol) and the reaction was stirred for 16 h at room temperature. The reaction was concentrated and the residue was purified by medium pressure revered phase chromagraphy (LiChroprep RP-18 Lobar (B) 25×310 mm—EMD chemicals 40-63 μm, ~70 g, 90/10 to 80/20 0.1% TFA-ACN) to afford 87.9 mg (82% yield) of example 8 as an orange film: $^1$NMR (300 MHz, DMSO-$d_6$) δ 8.46 (t, J=5.7 Hz, 2H), 7.96 (t, J=5.4 Hz, 2H), 3.16-3.73 (complex m, 74H), 2.28-2.32 (m, 2H). $^{13}$C NMR (75 MHz, DMSO-$d_6$)—multiple conformations—δ 170.1 (s), 169.9 (s) 169.8 (s), 165.1 (s), 146.0 (s), 126.2 (s). 71.2 (t), 69.7 (t), 69.6 (t), 69.5 (t), 66.7 (t), 58.0 (q), 38.2 (t), 36.2 (t). LCMS (15-95% gradient acetonitrile in 0.1% TFA over 10 min), single peak retention time=5.90 min on 250 mm column, $(M+H)^+$=1071, $(M+2H)^{2+}$=536. UV/vis (100 μM in PBS) $\lambda_{abs}$=438 nm. Fluorescence (100 nM) $\lambda_{ex}$=438 nm, $\lambda_{em}$=560 nm.

EXAMPLE 9

3,6-Diamino-$N^2$,$N^5$-bis(38-oxo-2,5,8,11,14,17,20,23,26,29,32,35-dodecaoxa-39-azahentetracontan-41-yl)pyrazine-2,5-dicarboxamide

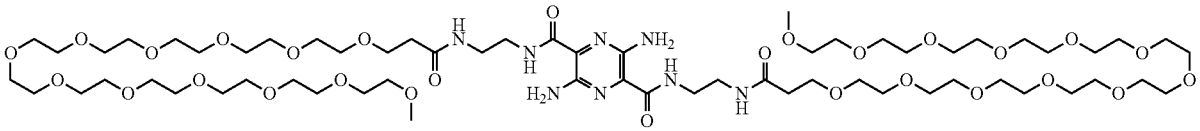

To a solution of Example 5 (53.1 mg, 0.10 mmol) in DMF (5 mL) was added TEA (114 mg, 1.13 mmol) and 2,5-dioxopyrrolidin-1-yl 2,5,8,11,14,17,20,23,26,29,32,35-dodecaoxaoctatriacontan-38-oate (144 mg, 0.21 mmol) in DMF (2.0 mL) and the resulting mixture was stirred for 16 h thereafter. The reaction was concentrated and the residue was purified by medium pressure revered phase chromagraphy (LiChroprep RP-18 Lobar (B) 25×310 mm—EMD chemicals 40-63 μm, ~70 g, 90/10 to 80/20 0.1% TFA-ACN) to afford 87.5 mg (61% yield) of example 9 as an orange film: $^1$NMR (300 MHz, DMSO-$d_6$) δ 8.48 (t, J=5.7 Hz, 2H), 7.96 (t, J=5.4 Hz, 2H), 7.80-7.86 (m, 2H), 5.94 (bm, 2H), 3.30-3.60 (complex m, 106H), 2.26-2.33 (m, 4H). $^{13}$C NMR (75 MHz, DMSO-$d_6$) δ 170.2 (s), 165.1 (s), 146.0 (s), 126.2 (s), 71.2 (t), 69.7 (t), 69.6 (t), 69.5 (t), 66.7 (t), 58.0 (q), 38.2 (t), 36.2 (t). LCMS (15-95% gradient acetonitrile in 0.1% TFA over 10 min), single peak retention time=5.90 min on 250 mm column, $(M+2H)^{2+}$=712. UV/vis (100 μM in PBS) $\lambda_{abs}$=449 nm. Fluorescence (100 nM) $\lambda_{ex}$=449 nm, $\lambda_{em}$=559 nm.

EXAMPLE 10

Bis(2-(PEG-5000)ethyl) 6-(2-(3,6-diamino-5-(2-aminoethylcarbamoyl)pyrazine-2-carboxamido)ethylamino)-6-oxohexane-1,5-diyldicarbamate

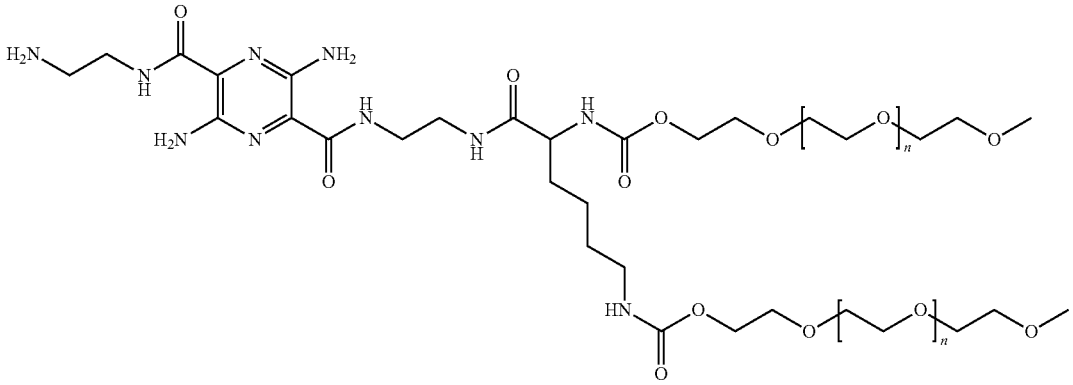

n~110-114
Overall MW~11,000

A solution of Example 5 (25 mg, 0.049 mmol) in DMF (30 mL) was treated with TEA (1 mL) and m-PEG2-NHS (1 g, 0.1 mmol) and the resulting mixture was stirred for 48 h at room temperature. The mixture was concentrated and the residue was partially purified by gel filtration chromatography (G-25 resin, water). The product was concentrated and further purified by reverse phase medium pressure chromatography (C18, 10-70% manual gradient acetonitrile in 0.1% TFA) to afford 137.8 mg (54% yield) of Example 10 as a tan waxy solid: Maldi MS m/z=11393.

EXAMPLE 11

(R)-2-(6-(bis(2-methoxyethyl)amino)-5-cyano-3-morpholinopyrazine-2-carboxamido)succinic acid

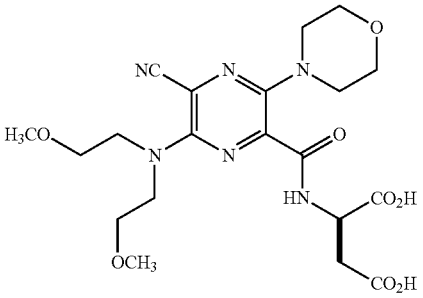

Step 1. Synthesis of 2-amino-5-bromo-3,6-dichloropyrazine

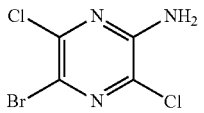

A solution of 2-amino-6-chloropyrazine (25 g, 193.1 mmol) in MeOH (500 mL) was treated with NBS (34.3 g, 193.1 mmol), portion-wise, over 1 hour. The resulting mixture was stirred for 16 hours thereafter. TLC analysis at this time shows a small amount of starting material remaining. Another 1.4 g NBS added and reaction heated to 50° C. for 2 hours. The mixture was then cooled to 38° C. and treated with NCS (25.8 g, 193.1 mmol). The reaction mixture was heated to 50° C. for 16 hours thereafter. The mixture was then cooled to room temperature and treated with water (500 mL). The precipitate was collected by filtration and dried in a vacuum dessicator to afford 45.4 g (97% yield) of 2-amino-5-bromo-3,6-dichloropyrazine as a white solid: $^{13}C$ NMR (75 MHz, $CDCl_3$) δ 149.9 (s), 145.6 (s), 129.6 (s), 121.5 (s). LCMS (15-95% gradient acetonitrile in 0.1% TFA over 10 min), single peak retention time=4.51 min on 30 mm column, $(M+H)^+$=244, $(M+H+ACN)^+$=285.

Step 2. Synthesis of 5-amino-3,6-dichloropyrazine-2-carbonitrile

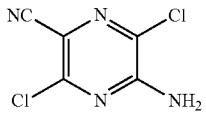

A mixture of CuCN (8.62 g, 96.3 mmol) and NaCN (4.72 g, 96.3 mmol) was heated under high vacuum to 90° C. The resulting mixture was subjected to three Argon/Vacuum cycles and placed under a final positive pressure of Argon. The mixture was allowed to cool to room temperature and DMF (150 mL) was added. The heterogenous mixture was heated to 130° C. for 2.5 hours. To the resulting homogeneous mixture of sodium dicyanocuprate was added a solution of the product from step 1 (15.6 g, 64.2 mmol) dissolved in DMF (150 mL), dropwise, over 1 hour. The temperature was gradually raised to 150° C. and the resulting mixture was stirred at this temperature for 10 hours thereafter. The reaction was then allowed to cool to room temperature and poured into water (1 L). The resulting mixture was extracted with EtOAc (3×) and the combined extracts were filtered to remove a flocculant dark solid, washed with brine, dried ($Na_2SO_4$), filtered again and concentrated. Purification by flash column chromatography ($SiO_2$, 10/1 hexanes-EtOAc to 3/1) to afford 6.70 g (55% yield) of the nitrile product as a tan solid: $^{13}C$ NMR (75 MHz, $CDCl_3$) δ 153.9 (s), 149.1 (s), 131.7 (s), 115.4 (s), 111.0 (s). GCMS (Inj. temperature=280° C., 1.0 mL/min helium flow rate, temperature program: 100° C. (2 min hold), ramp to 300° C. @ 10° C./min (2 min hold), major peak retention time=16.556 min, m/z (EI)=188, 190.

Step 3. Synthesis of 5-amino-3-(bis(2-methoxyethyl)amino)-6-chloropyrazine-2-carbonitrile

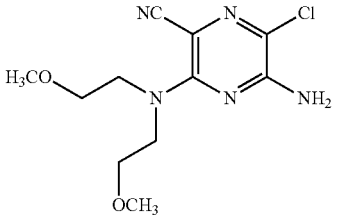

To the product from step 2 (1.00 g, 5.29 mmol) in ACN (20 mL) was added bis(2-methoxyethyl)amine (3.0 mL, 2.71 g, 20.3 mmol) and the reaction mixture was heated to 70° C. for 16 hours thereafter. The reaction was cooled and concentrated. The residue was partitioned with EtOAc and water. The organic layer was separated and the aqueous was extracted again with EtOAc. The combined organic extracts were washed with brine, dried ($Na_2SO_4$), filtered and concentrated. Purification by flash column chromatography ($SiO_2$, 10/1 hexanes-EtOAc to 1/1) afforded 950 mg (63% yield) of the desired adduct as a yellow solid: $^1$NMR (300 MHz, $CDCl_3$) δ 7.47 (bs, 2H), 3.77 (t, J=5.7 Hz, 4H), 3.52 (t, J=5.4 Hz, 4H), 3.25 (s, 6H). $^{13}C$ NMR (75 MHz, $CDCl_3$) δ 154.7 (s), 152.0 (s), 120.9 (s), 119.5 (s), 95.8 (s), 71.0 (t), 59.1 (q), 50.0 (t). LCMS (50-95% gradient acetonitrile in 0.1% TFA over 10 min), single peak retention time=4.91 mm on 250 mm column, $(M+H)^+$=286, $(M+Na)^+$=308, $(M+Na+ACN)^+$=349.

Step 4. Synthesis of 3-(bis(2-methoxyethyl)amino)-5-bromo-6-chloropyrazine-2-carbonitrile

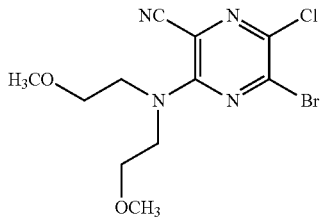

To the product from step 3 (1.39 g, 4.88 mmol) in 48% hydrobromic acid (20 mL) at 0° C. (ice-salt bath), was added a solution of sodium nitrite (673 mg, 9.75 mmol) in water (10 mL) dropwise over 30 min. The resulting mixture was stirred at 0-5° C. for 1 h and poured into a stirred solution of $CuBr_2$ (1.64 g, 7.34 mmol) in water (100 mL). The resulting mixture was stirred for 16 h at room temperature thereafter. The mixture was extracted with EtOAc (3×). The combined organic layers were dried ($Na_2SO_4$), filtered and concentrated. Purification by flash column chromatography ($SiO_2$, 50/1 CHCl3-MeOH) afforded 1.00 g (58% yield) of the bromide as a orange-brown solid: $^1$NMR (300 MHz, $CDCl_3$) δ 3.99 (t, J=5.4 Hz, 4H), 3.64 (t, J=5.4 Hz, 4H), 3.35 (s, 6H). $^{13}C$ NMR (75 MHz, $CDCl_3$) δ 152.8 (s), 140.8 (s), 133.4 (s), 117.2 (s), 108.3 (s), 70.4 (t), 59.1 (t), 50.5 (q). LCMS (50-95% gradient acetonitrile in 0.1% TFA over 10 min), single peak retention time=4.55 min on 250 mm column, $(M+H)^+$=349, 351.

Step 5. Synthesis of 3-(bis(2-methoxyethyl)amino)-6-chloro-5-(furan-2-yl)pyrazine-2-carbonitrile

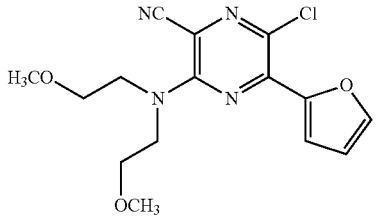

A mixture of the product from step 4 (1.0 g, 2.87 mmol), 2-furanboronic acid (643 mg, 5.75 mmol), $Cs_2CO_3$ (3.31 g, 10.2 mmol), TFP (35 mol %, 236 mg, 1.02 mmol), and $Pd_2dba_3$-$CHCl_3$ (5 mol %, 10 mol % Pd, 150 mg) was subjected to 3 vacuum/Argon cycles and placed under a positive pressure of Argon. Anhydrous dioxane (50 mL) was added and the reaction mixture was heated to 75° C. for 16 h thereafter. The reaction mixture was cooled to room temperature, diluted with EtOAc (100 mL) and filtered through a medium frit. Concentration and purification of the residue by flash chromatography ($SiO_2$, 50/1 $CHCl_3$-MeOH) afforded the 757 mg of the furan adduct (78% yield) as a tan powder: LCMS (5-95% gradient acetonitrile in 0.1% TFA over 10 min), single peak retention time=6.41 min on 250 mm column, $(M+H)^+$=337.

Step 6. Synthesis of 6-(bis(2-methoxyethyl)amino)-3-chloro-5-cyanobyrazine-2-carboxylic acid

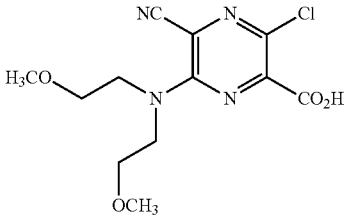

To a well stirred mixture of ACN (11 mL), CCl4 (7 mL), and water (11 mL) were added sodium periodate (1.07 g, 5.00 mmol) and RuO2.$H_2O$ (13.3 mg, 0.10 mmol), sequentially. The resulting mixture was stirred vigorously at room temperature for 30 min and treated with sodium bicarbonate (2.10 g, 25.0 mmol) followed by water (5 mL). Vigorous stirring for another 15 minutes was followed by the addition of a solution of the product from Step 5 (276 mg, 0.82 mmol) dissolved in ACN (1 mL). The green mixture was stirred at room temperature for 5.5 h. The mixture was transferred to a separatory funnel and extracted with EtOAc. The aqueous layer was adjusted to pH~3.5 and extracted again with EtOAc (2×). The combined extracts were washed with 20% sodium bisulfite and brine and dried ($Na_2SO_4$). Filtration and concentration afforded 140 mg (54% yield) of carboxylic acid as a pale yellow solid: LCMS (5-95% gradient acetonitrile in 0.1% TFA over 10 min), single peak retention time=5.05 min on 250 mm column, $(M+H)^+$=315.

Step 7. Synthesis of (R)-dibenzyl 2-(6-(bis(2-methoxyethyl)amino)-3-chloro-5-cyanopyrazine-2-carboxamido)succinate

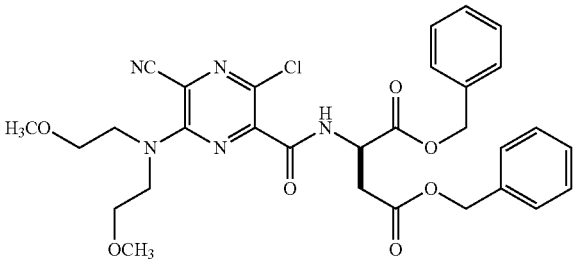

A mixture of the product from step 6 (140 mg, 0.45 mmol), EDC.HCl (128 mg, 0.67 mmol) and HOBt.$H_2O$ (102 mg, 0.67 mmol) in anhydrous DMF (25 mL) was stirred together at room temperature for 30 min. To this stirred mixture was added (R)-dibenzyl 2-aminosuccinate p-TsOH salt (213 mg, 0.44 mmol) followed by TEA (1 mL). The resulting mixture was stirred for 16 h thereafter. The reaction mixture was concentrated and partitioned with EtOAc and saturated sodium bicarbonate solution. The EtOAc layer was separated and washed with saturated sodium bicarbonate and brine, dried ($Na_2SO_4$), filtered and concentrated to afford 240 mg (88% yield) of the pyrazine amide as an orange foam: LCMS (15-95% gradient acetonitrile in 0.1% TFA over 10 min), single peak retention time=8.76 min on 250 mm column, $(M+H)^+$=610, $(M+Na)^+$=632.

Step 8. (R)-dibenzyl 2-(6-(bis(2-methoxyethyl) amino)-5-cyano-3-morpholinopyrazine-2-carboxamido)succinate

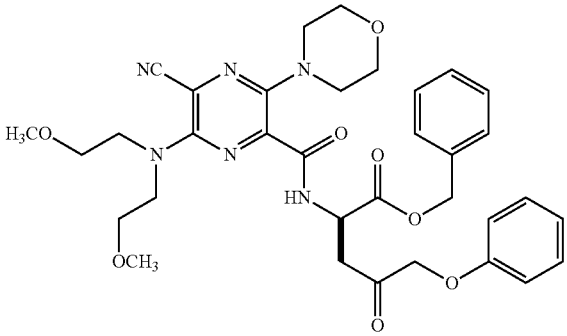

To the product from step 7 (240 mg, 0.39 mmol) was added morpholine (5 mL). The reaction mixture was heated to 70° C. for 2 h. The mixture was cooled and concentrated. The residue was partitioned with EtOAc and water. The EtOAc layer was separated and washed with saturated sodium bicarbonate and brine. The EtOAc layer was dried ($Na_2SO_4$), filtered and concentrated. Purification by flash column chromatography ($SiO_2$, 3:1 to 1:1 hexanes-EtOAc) afforded 199 mg (75% yield) of the morpholine adduct as an orange foam: LCMS (15-95% gradient acetonitrile in 0.1% TFA over 10 min), single peak retention time=8.76 min on 250 mm column, $(M+H)^+$=661, $(M+Na)^+$=683.

Step 9. Synthesis of Example 11

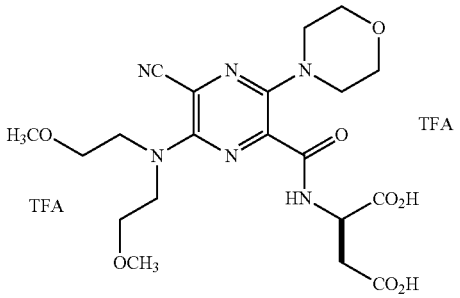

The dibenzyl ester (115 mg, 0.17 mmol) in THF (10 mL) was added 1.0 N sodium hydroxide (4 mL). The mixture was stirred for 1 h at room temperature. The pH was adjusted to ~2 with 1.0 N HCl and the solution was concentrated. Purification of the residue by medium pressure reversed phase chromatography (LiChroprep RP-18 Lobar (B) 25×310 mm EMD chemicals 40-63 μm, ~70 g, 90/10 to 50/50 0.1% TFA-ACN) afforded 32 mg (27% yield) of example 11 as an orange solid: LCMS (15-95% gradient acetonitrile in 0.1% TFA over 10 min), single peak retention time=4.47 min on 250 mm column, $(M+H)^+$=481. UV/vis (100 μM in PBS) $\lambda_{abs}$=438 nm. Fluorescence (100 nM) $\lambda_{ex}$=449 nm, $\lambda_{em}$=570 nm.

EXAMPLE 12

Protocol for Assessing Renal Function

Figure 2:
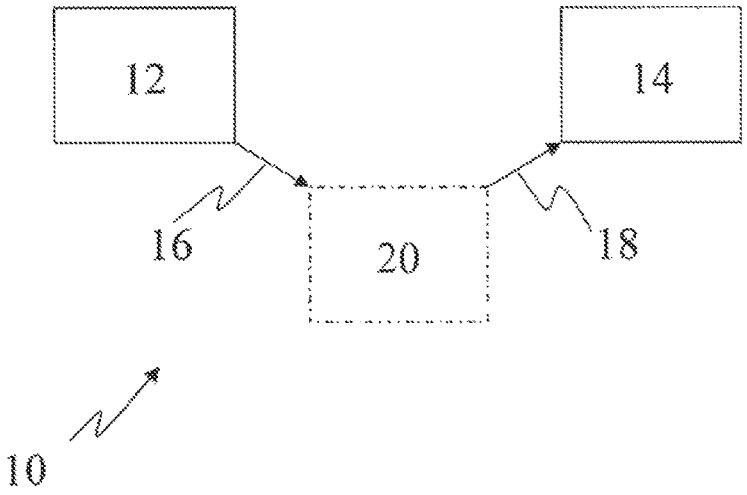
FIG. 2 illustrates a block diagram of an assembly for assessing renal function.

An example of an in vivo renal monitoring assembly 10 is shown in FIG. 2 and includes a light source 12 and a data processing system 14. The light source 12 generally includes or is interconnected with an appropriate device for exposing at least a portion of a patient's body to light therefrom. Examples of appropriate devices that may be interconnected with or be a part of the light source 12 include, but are not limited to, catheters, endoscopes, fiber optics, ear clips, hand bands, head bands, forehead sensors, surface coils, and finger probes. Indeed, any of a number of devices capable of emitting visible and/or near infrared light of the light source may be employed in the renal monitoring assembly 10.

Still referring to FIG. 2, the data processing system 14 of the renal monitoring assembly 10 may be any appropriate system capable of detecting spectral energy and processing data indicative of the spectral energy. For instance, the data processing system 14 may include one or more lenses (e.g., to direct and/or focus spectral energy), one or more filters (e.g., to filter out undesired wavelengths of spectral energy), a photodiode (e.g., to collect the spectral energy and convert the same into electrical signal indicative of the detected spectral energy), an amplifier (e.g., to amplify electrical signal from the photodiode), and a processing unit (e.g., to process the electrical signal from the photodiode). This data processing system 14 is preferably configured to manipulate collected spectral data and generate an intensity/time profile and/or a concentration/time curve indicative of renal clearance of a pyrazine derivative of the present invention from the patient 20. Indeed, the data processing system 14 may be configured to generate appropriate renal function data by comparing differences in manners in which normal and impaired cells remove the pyrazine derivative from the bloodstream, to determine a rate or an accumulation of the pyrazine derivative in organs or tissues of the patient 20, and/or to provide tomographic images of organs or tissues having the pyrazine derivative associated therewith.

In one protocol for determining renal function, an effective amount of a pyrazine derivative of the invention is administered to the patient (e.g., in the form for a pharmaceutically acceptable composition). At least a portion of the body of the patient 20 is exposed to visible and/or near infrared light from the light source 12 as indicated by arrow 16. For instance, the light from the light source 12 may be delivered via a fiber optic that is affixed to an ear of the patient 20. The patient may be exposed to the light from the light source 12 before or after administration of the pyrazine derivative to the patient 20. In some cases, it may be beneficial to generate a background or baseline reading of light being emitted from the body of the patient 20 (due to exposure to the light from the light source 12) before administering the pyrazine derivative to the patient 20. When the pyrazine derivative that is in the body of the patient 20 is exposed to the light from the light source 12, the pyrazine derivative emanates light (indicated by arrow 18) that is detected/collected by the data processing system 14. Initially, administration of the pyrazine derivative to the patient 20 generally enables an initial spectral signal indicative of the initial content of the pyrazine derivative in the patient 20. The spectral signal then tends to decay as a function of time as the pyrazine derivative is cleared from the patient 20. This decay in the spectral signal as a function of time is indicative of the patient's renal function. For example, in a first patient exhibiting healthy/normal renal function, the spectral signal may decay back to a baseline in a time of T. However, a spectral signal indicative of a second patient exhibiting deficient renal function may decay back to a baseline in a time of T+4 hours. As such, the patient 20 may be exposed to the light from the light source 12 for any amount of time appropriate for providing the desired renal function data. Likewise, the data processing system 14 may be allowed to collect/detect spectral energy for any amount of time appropriate for providing the desired renal function data.

REFERENCES

1. Nally, J. V. Acute renal failure in hospitalized patients. Cleveland Clinic Journal of Medicine 2002, 69(7), 569-574.
2. C. A. Rabito, L. S. T. Fang, and A. C. Waltman. Renal function in patients at risk with contrast material-induced acute renal failure: Noninvasive real-time monitoring. Radiology 1993, 186, 851-854.
3. N. L. Tilney, and J. M. Lazarus. Acute renal failure in surgical patients: Causes, clinical patterns, and care. Surgical Clinics of North America 1983, 63, 357-377.
4. B. E. VanZee, W. E. Hoy, and J. R. Jaenike. Renal injury associated with intravenous pyelography in non-diabetic and diabetic patients. Annals of Internal Medicine 1978, 89, 51-54.
5. S. Lundqvist, G. Edbom, S. Groth, U. Stendahl, and S.-O. Hietala. Iohexol clearance for renal function measurement in gynecologic cancer patients. Acta Radiologica 1996, 37, 582-586.
6. P. Guesry, L. Kaufman, S. Orloff, J. A. Nelson, S. Swann, and M. Holliday. Measurement of glomerular filtration rate by fluorescent excitation of non-radioactive meglumine iothalamate. Clinical Nephrology 1975, 3, 134-138).
7. C. C. Baker et al. Epidemiology of Trauma Deaths. American Journal of Surgery 1980, 144-150.
8. R. G. Lobenhoffer et al. Treatment Results of Patients with Multiple Trauma: An Analysis of 3406 Cases Treated Between 1972 and 1991 at a German Level I Trauma Center. Journal of Trauma 1995, 38, 70-77.
9. J. Coalson, Pathology of Sepsis, Septic Shock, and Multiple Organ Failure. In New Horizons: Multiple Organ Failure, D. J. Bihari and F. B. Cerra, (Eds). Society of Critical Care Medicine, Fullerton, Calif., 1986, pp. 27-59.
10. F. B. Cerra, Multiple Organ Failure Syndrome. In New Horizons: Multiple Organ Failure, D. J. Bihari and F. B. Cerra, (Eds). Society of Critical Care Medicine, Fullerton, Calif., 1989, pp. 1-24.
11. R. Muller-Suur, and C. Muller-Suur. Glomerular filtration and tubular secretion of $MAG_3$ in rat kidney. Journal of Nuclear Medicine 1989, 30, 1986-1991).
12. P. D. Dollan, E. L. Alpen, and G. B. Theil. A clinical appraisal of the plasma concentration and endogenous clearance of creatinine. American Journal of Medicine 1962, 32, 65-79.
13. J. B. Henry (Ed). Clinical Diagnosis and Management by Laboratory Methods, 17th Edition, W.B. Saunders, Philadelphia, Pa., 1984.
14. F. Roch-Ramel, K. Besseghir, and H. Murer. Renal excretion and tubular transport of organic anions and cations. In Handbook of Physiology, Section 8, Neurological Physiology, Vol. II, E. E. Windhager, Editor, pp. 2189-2262. Oxford University Press: New York, 1992
15. D. L. Nosco and J. A. Beaty-Nosco. Chemistry of technetium radiopharmaceuticals 1: Chemistry behind the development of technetium-99m compounds to determine kidney function. Coordination Chemistry Reviews 1999, 184, 91-123.
16. P. L. Choyke, H. A. Austin, and J. A. Frank. Hydrated clearance of gadolinium-DTPA as a measurement of glomerular filtration rate. Kidney International 1992, 41, 1595-1598.
17. N. Lewis, R. Kerr, and C. Van Buren. Comparative evaluation of urographic contrast media, inulin, and $^{99m}$Tc-DTPA clearance methods for determination of glomerular filtration rate in clinical transplantation. Transplantation 1989, 48, 790-796).
18. W. N. Tauxe. Tubular Function. In Nuclear Medicine in Clinical Urology and Nephrology, W. N. Tauxe and E. V. Dubovsky, Editors, pp. 77-105, Appleton Century Crofts: East Norwalk, 1985.
19. A. R. Fritzberg et al. Mercaptoacetylglycylglycyglycine. Journal of Nuclear Medicine 1986, 27, 111-120.
20. G. Ekanoyan and N. W. Levin. In Clinical Practice Guidelines for Chronic Kidney Disease: Evaluation, Classification, and Stratification (K/DOQI). National Kidney Foundation: Washington, D.C. 2002, pp. 1-22.
21. Ozaki, H. et al. Sensitization of europium(III) luminescence by DTPA derivatives. Chemistry Letters 2000, 312-313.
22. Rabito, C. Fluorescent agents for real-time measurement of organ function. U.S. patent 2002; U.S. Pat. No. 6,440, 389.
23. R. Rajagopalan, R. et al. Polyionic fluorescent bioconjugates as composition agents for continuous monitoring of renal function. In Molecular Imaging: Reporters, Dyes, Markers, and Instrumentation, A. Priezzhev, T. Asakura, and J. D. Briers, Editors, Proceedings of SPIE, 2000, 3924.

24. Dorshow, R. B. et al. Noninvasive renal function assessment by fluorescence detection. In Biomedical Optical Spectroscopy and Diagnostics, Trends in Optics and Photonics Series 22, E. M Sevick-Muraca, J. A. Izatt, and M. N. Ediger, Editors, pp. 54-56, Optical Society of America, Washington D.C., 1998.
25. Shirai, K. et al Synthesis and fluorescent properties of 2,5-diamino-3,6-dicyanopyrazine dyes. Dyes and Pigments 1998, 39(1), 49-68.
26. Kim, J. H. et al. Self-assembling of aminopyrazine fluorescent dyes and their solid state spectra. Dyes and Pigments 1998, 39(4), 341-357.
27. Berlin, G. B. The pyrazines. In The Chemistry of Heterocyclic Compounds. A. Weissberger and E. C. Taylor, Eds. John Wiley & Sons, New York: 1982.
28. Donald, D. S. Synthesis of 3,5-diaminopyrazinoic acid from 3,5-diamino-2,6-dicyanopyrazine and intermediates. U.S. patent 1976; U.S. Pat. No. 3,948,895.
29. Donald, D. S. Diaminosubstituted dicyanopyrzines and process. U.S. patent 1974; U.S. Pat. No. 3,814,757.
30. Muller et al. Eds, Medical Optical Tomography, SPIE Volume IS11, 1993.
31. R. B. Dorshow et al. Non-Invasive Fluorescence Detection of Hepatic and Renal Function, Bull. Am. Phys. Soc. 1997, 42, 681.
32. R. B. Dorshow et al. Monitoring Physiological Function by Detection of Exogenous Fluorescent Contrast Agents. In Optical Diagnostics of Biological Fluids IV, A. Priezzhevand T. Asakura, Editors, Proceedings of SPIE 1999, 3599, 2-8).

What is claimed is:

1. A pharmaceutical composition comprising a compound of Formula I, wherein:

Formula I

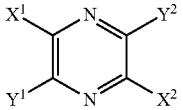

each of $X^1$ and $X^2$ is independently —$CO_2R^1$, —$CONR^2R^3$, —*CO*(*AA*) or —CONH(PS);

each of $Y^1$ and $Y^2$ is independently —$NR^4R^5$ or

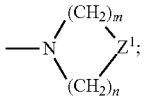

$Z^1$ is a single bond, —$CR^{18}R^{19}$—, —O—, —$NR^{20}$—, —$NCOR^{21}$—, —S—, —SO—, or —$SO_2$—;

$R^1$ is —$CH_2(CHOH)_aR^{44}$, —$CH_2(CHOH)_aCO_2H$, —$(CHCO_2H)_aCO_2H$, —$(CH_2CH_2O)_cR^{49}$, —$(CH_2)_aSO_3H$, —$(CH_2)_aSO_3^-$, —$(CH_2)_aNHSO_3H$, —$(CH_2)_aNHSO_3^-$, —$(CH_2)_aPO_3H_2$, —$(CH_2)_aPO_3H^-$, or —$(CH_2)_aPO_3^=$;

each of $R^{44}$ and $R^{49}$ is independently —H or —$CH_3$;

each of $R^2$ to $R^5$ and $R^{18}$ to $R^{21}$ is independently —H, —$CH_2(CHOH)_aR^{44}$, —$CH_2(CHOH)_aCO_2H$, —$(CHCO_2H)_aCO_2H$, —$(CH_2CH_2O)_cR^{49}$, —$(CH_2)_aSO_3H$, —$(CH_2)_aSO_3^-$, —$(CH_2)_aNHSO_3H$, —$(CH_2)_aNHSO_3^-$, —$(CH_2)_aPO_3H_2$, —$(CH_2)_aPO_3H^-$, or —$(CH_2)_aPO_3^=$;

each of $R^{44}$ and $R^{49}$ is independently —H or —$CH_3$;

(*AA*) *comprises a single natural or unnatural amino acid or a polypeptide chain comprising two or more natural and/or unnatural amino acids linked together by peptide bonds, and each instance of AA may be the same or different than each other instance;*

(PS) is a sulfated or non-sulfated polysaccharide chain comprising one or more monosaccharide units connected by glycosidic linkages; and 'a' is an integer from 1 to 10, 'c' is an integer from 1 to 100, and each of 'm' and 'n' independently is an integer from 1 to 3.

2. The pharmaceutical composition as recited in claim 1 further comprising a pharmaceutically acceptable excipient.

3. The pharmaceutical composition as recited in claim 2 wherein the pharmaceutically acceptable excipient is chosen from a diluent, preservative, solubilizer, emulsifier, adjuvant, and carrier.

4. The pharmaceutical composition as recited in claim 2 wherein the pharmaceutical acceptable excipient is phosphate buffered saline.

5. The pharmaceutical composition as recited in claim 2 wherein the pharmaceutical composition is a liquid.

*6. The pharmaceutical composition as recited in claim 1, wherein at least one of $X^1$ and $X^2$ is —CONH(PS) or —CO(AA).*

*7. The pharmaceutical composition as recited in claim 1, wherein both $X^1$ and $X^2$ are —CO(AA).*

*8. The pharmaceutical composition as recited in claim 7, wherein each instance of AA is one or more of D-α-amino acids.*

*9. The pharmaceutical composition as recited in claim 8, wherein each instance of AA is a single D-α-amino acid.*

*10. The pharmaceutical composition as recited in claim 8, wherein AA is selected from the group consisting of D-aspartic acid, D-asparagine, D-arginine, D-histidine, D-lysine, D-glutamic acid, D-glutamine, D-serine, and D-homoserine.*

*11. The pharmaceutical composition as recited in claim 8, wherein AA is selected from the group consisting of D-serine and D-aspartic acid.*

*12. The pharmaceutical composition as recited in claim 8, wherein AA is D-serine.*

*13. The pharmaceutical composition as recited in claim 9, wherein AA is D-serine, $Y^1$ and $Y^2$ are each —$NR^4R^5$ with $R^4$=$R^5$=H.*

*14. The pharmaceutical composition as recited in claim 7, wherein each instance of AA is one or more of L-α-amino acids.*

*15. The pharmaceutical composition as recited in claim 14, wherein each instance of AA is a single L-α-amino acid.*

*16. The pharmaceutical composition as recited in claim 14, wherein AA is selected from the group consisting of L-aspartic acid, L-asparagine, L-arginine, L-histidine, L-lysine, L-glutamic acid, L-glutamine, L-serine, and L-homoserine.*

*17. The pharmaceutical composition as recited in claim 14, wherein AA is selected from the group consisting of L-serine and L-aspartic acid.*

*18. The pharmaceutical composition as recited in claim 14, wherein AA is L-serine.*

*19. The pharmaceutical composition as recited in claim 15, wherein AA is L-serine, $Y^1$ and $Y^2$ are each —$NR^4R^5$ with $R^4$=$R^5$=H.*

*20. The pharmaceutical composition as recited in claim 4, wherein $X^1$ and $X^2$ are —CO(AA), AA is a single D-α-amino acid that is D-serine, $Y^1$ and $Y^2$ are each —$NR^4R^5$ with $R^4$=$R^5$=H.*

*21. The pharmaceutical composition as recited in claim 4, wherein $X^1$ and $X^2$ are —CO(AA), AA is a single L-α-amino acid that is L-serine, $Y^1$ and $Y^2$ are each —$NR^4R^5$ with $R^4$=$R^5$=H.*

* * * * *